(12) United States Patent
Pressly, Sr. et al.

(10) Patent No.: US 7,303,547 B2
(45) Date of Patent: *Dec. 4, 2007

(54) INTERCHANGEABLE NEEDLE SAFETY SYRINGE

(75) Inventors: William B. S. Pressly, Sr., Greer, SC (US); Charles A. Vaughn, Sr., Greenville, SC (US); G. Samuel Brockway, Lawrenceville, GA (US); Thomas R. Ellis, Lawrenceville, GA (US)

(73) Assignee: MedSafe Technologies LLC, Lawrenceville, GA (US)

( * ) Notice: Subject to any disclaimer, the term of this patent is extended or adjusted under 35 U.S.C. 154(b) by 50 days.

This patent is subject to a terminal disclaimer.

(21) Appl. No.: 11/374,858

(22) Filed: Mar. 14, 2006

(65) Prior Publication Data

US 2006/0229556 A1 Oct. 12, 2006

Related U.S. Application Data

(63) Continuation of application No. 09/913,698, filed as application No. PCT/US00/04216 on Feb. 18, 2000, now Pat. No. 7,014,622.

(60) Provisional application No. 60/120,622, filed on Feb. 18, 1999.

(51) Int. Cl.
*A61M 5/00* (2006.01)

(52) U.S. Cl. ..................................... 604/110
(58) Field of Classification Search ............. 604/110, 604/111, 192–198, 181, 187, 268, 228, 207, 604/218, 222

See application file for complete search history.

(56) References Cited

U.S. PATENT DOCUMENTS

| | | | |
|---|---|---|---|
| 3,974,832 A | 8/1976 | Kruck | |
| 4,927,414 A | 5/1990 | Kulli | |
| 5,114,410 A | 5/1992 | Caralt Battle | |
| 5,201,710 A | 4/1993 | Caselli | |
| 5,211,629 A | 5/1993 | Pressly et al. | |
| 5,267,976 A | 12/1993 | Guerineau et al. | |

(Continued)

OTHER PUBLICATIONS

ISA/US, International Search Report, PCT/US00/004216, May 30, 2000, 1 page.

*Primary Examiner*—Matthew F. DeSanto
(74) *Attorney, Agent, or Firm*—J. Bennett Mullinax, LLC

(57) ABSTRACT

The present invention is a safety syringe for use with a plurality of interchangeable needles. The plurality of needles may be inserted by the user into the safety syringe for use. In operations, the user selects the desired needle, e.g., a needle having a particular gauge or size or of a particular type. The user inserts the needle (14) into a safety syringe (10) comprising a barrel (6), a needle assembly area (18) located within or attached to the barrel and a plunger (66). The needle couples to the syringe by a number of means. For instance, a locking mechanism (20, 22) may be used by which a needle hub located within the needle assembly has an area adapted to mate with a corresponding area on the needle. Or, the needle may be formed as part of a separate needle assembly, whereby the user will place the entire needle assembly onto the end of the syringe barrel. During use, the user operates the syringe like other safety syringe, using one hand to depress the plunger, which ultimately causes a spring to propel the needle into the barrel of the syringe.

2 Claims, 19 Drawing Sheets

U.S. PATENT DOCUMENTS

| | | |
|---|---|---|
| 5,304,137 A | 4/1994 | Fluke |
| 5,336,198 A | 8/1994 | Silver et al. |
| 5,613,952 A | 3/1997 | Pressly et al. |
| 5,782,803 A | 7/1998 | Jentzen |
| 5,843,034 A | 12/1998 | Redfern et al. |
| 5,902,269 A | 5/1999 | Jentzen |
| 6,074,370 A | 6/2000 | Pressly, Sr. et al. |

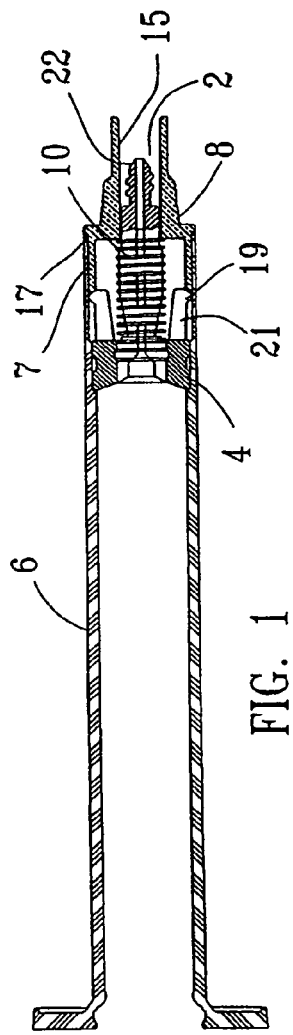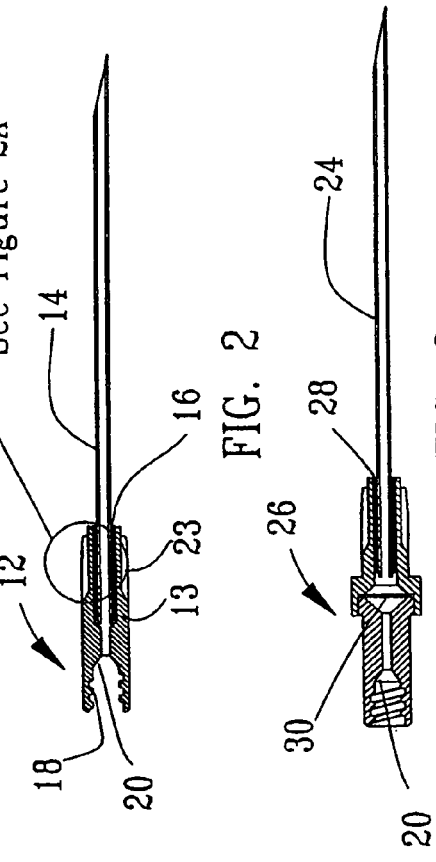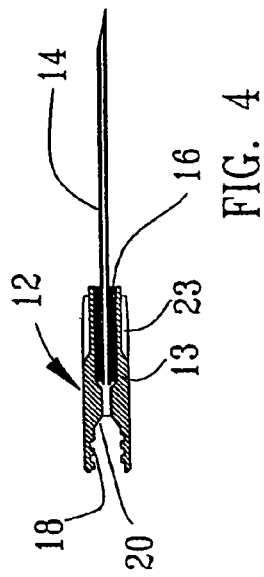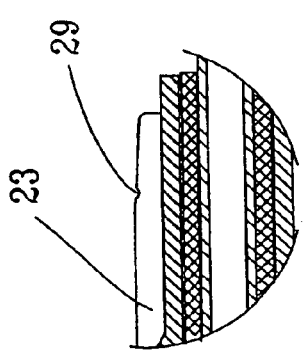

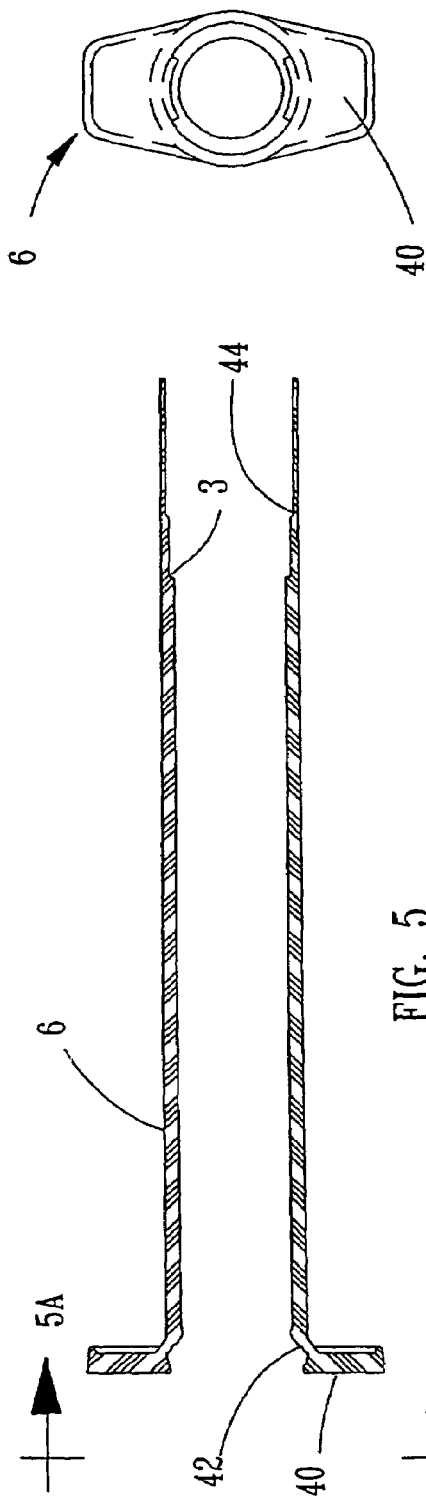
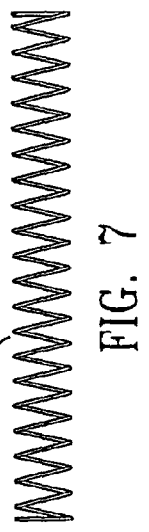
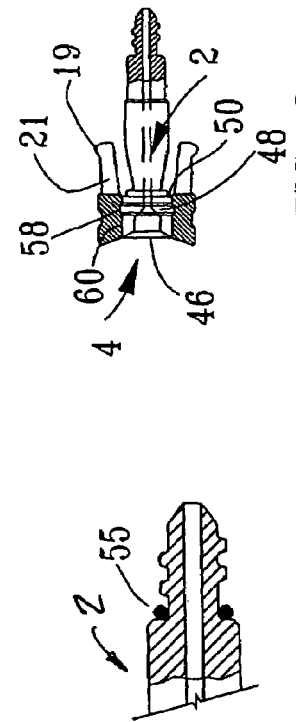
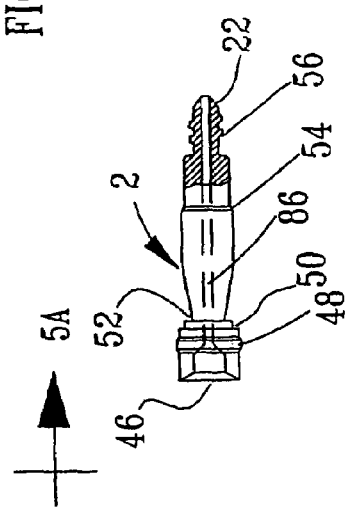

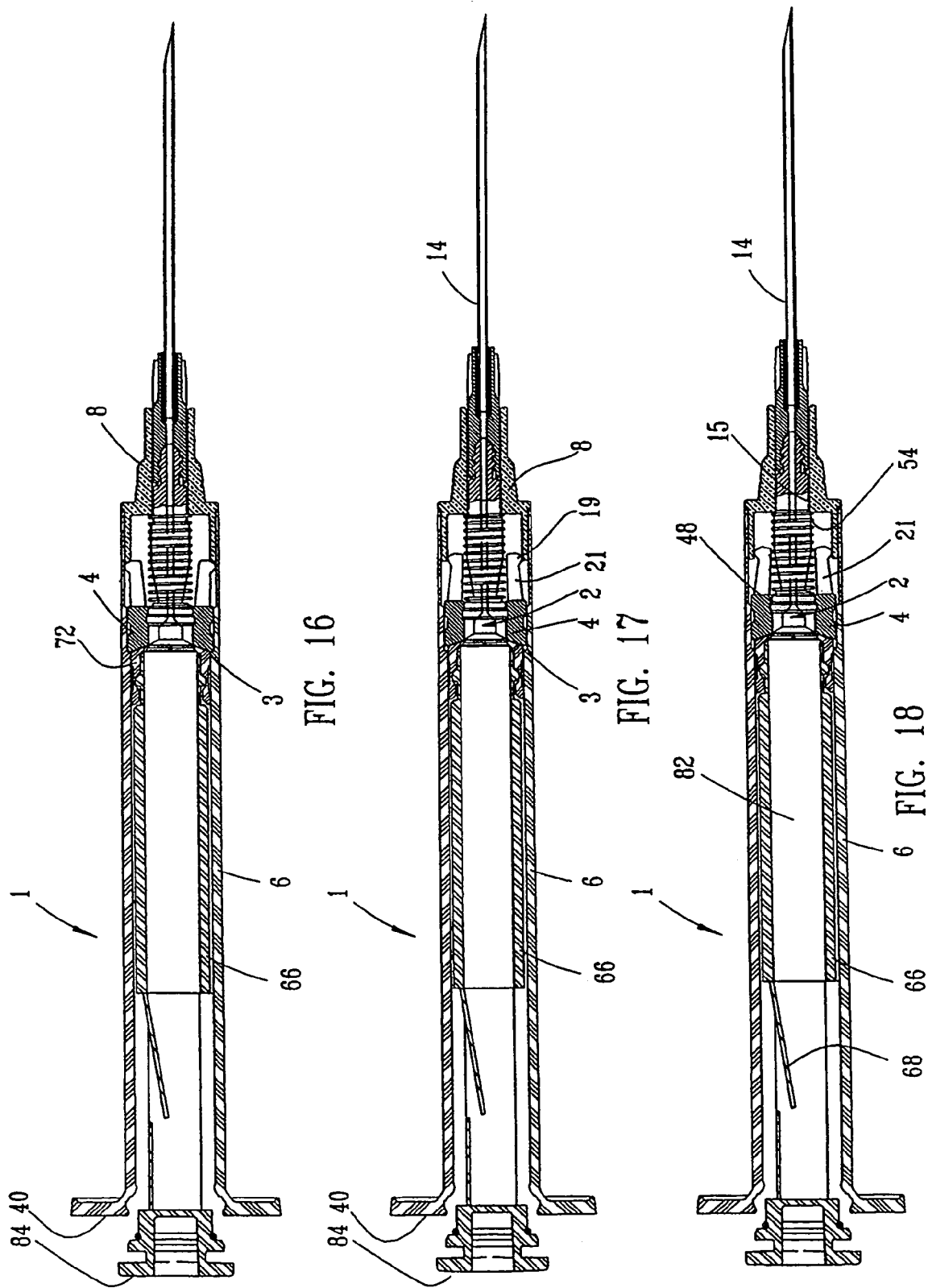

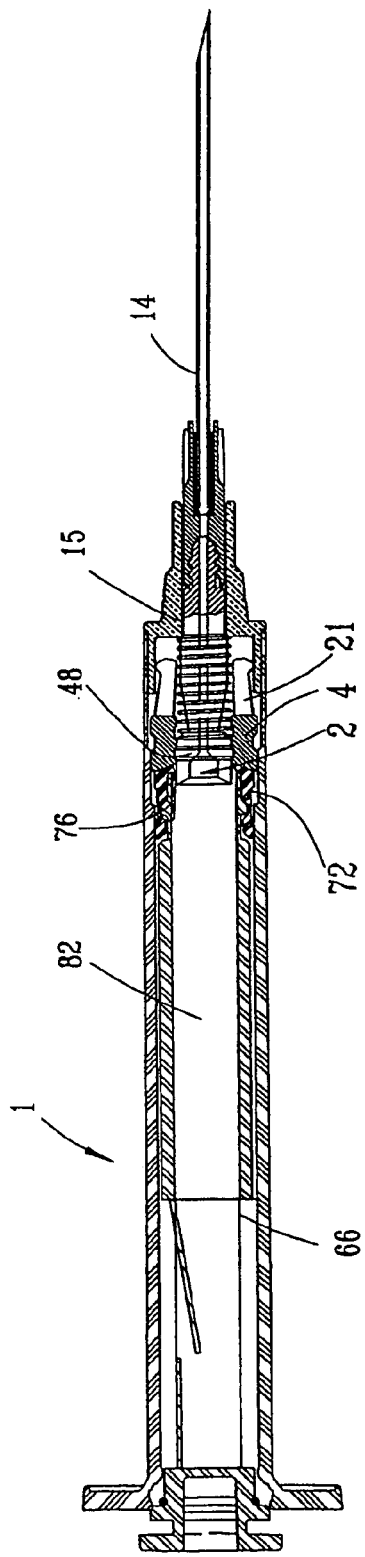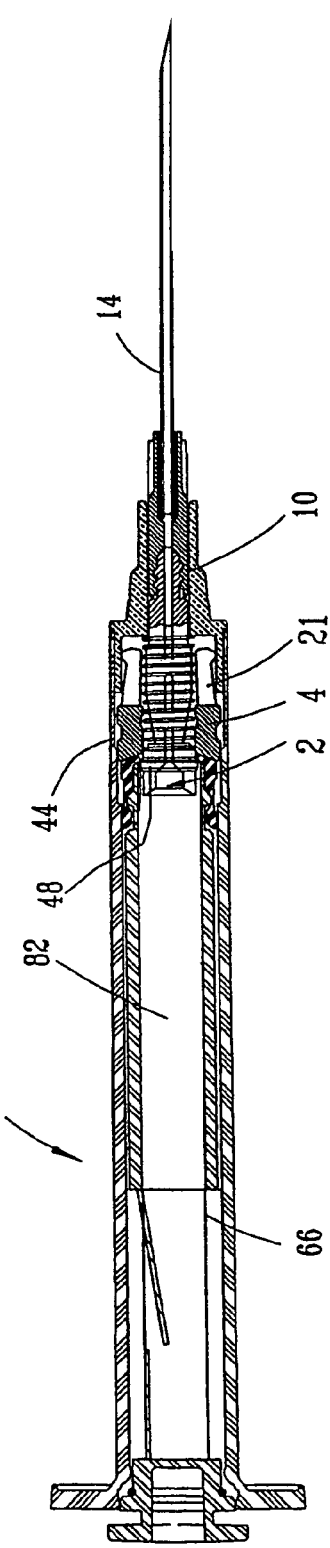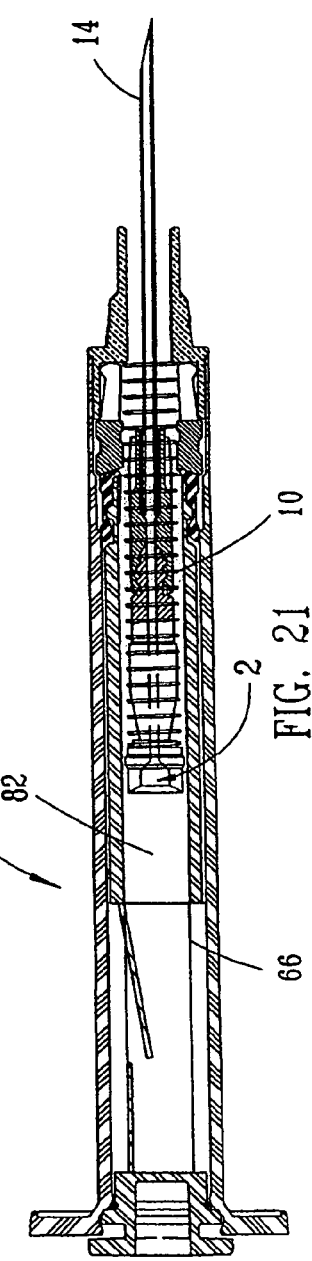

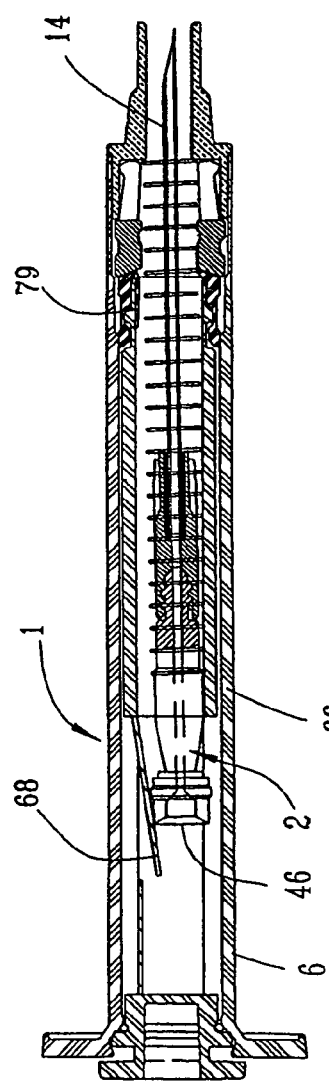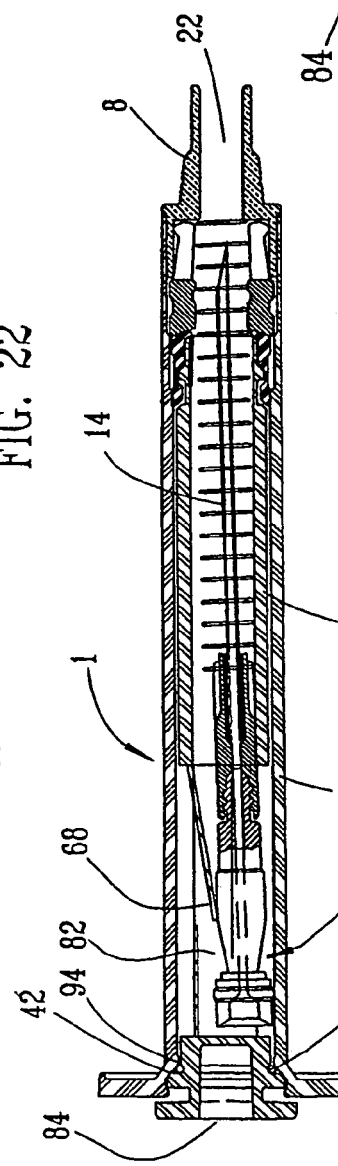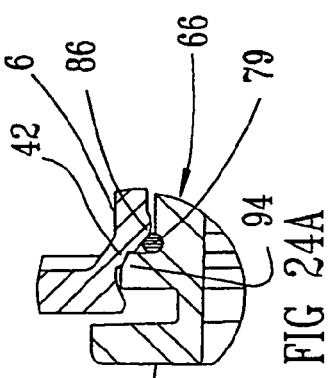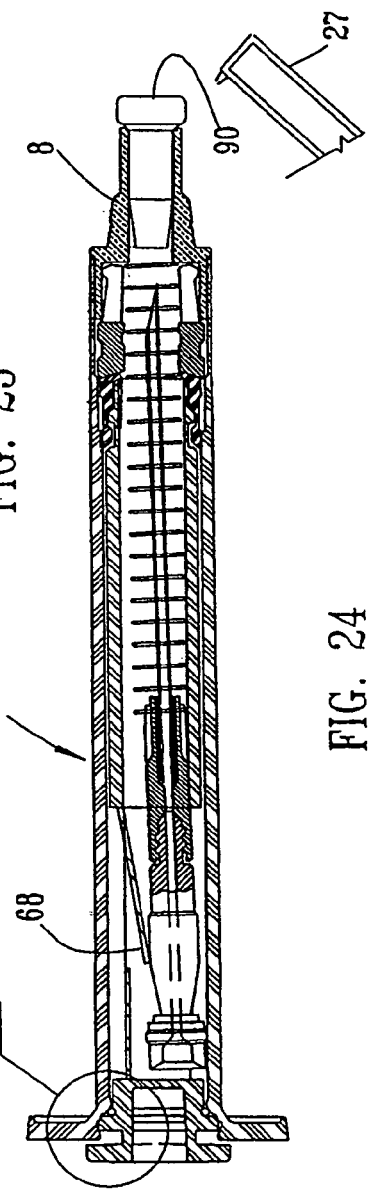
FIG. 22
FIG. 23
FIG. 24A
FIG. 24

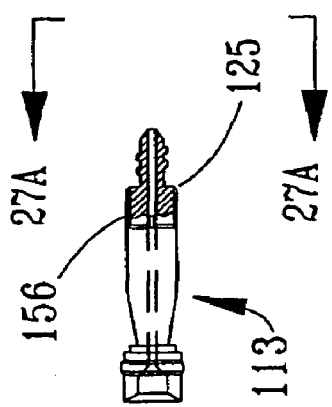
FIG. 27
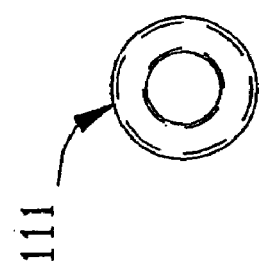
FIG. 28A
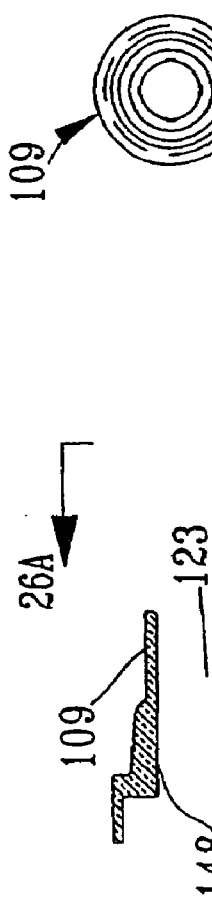
FIG. 26A
FIG. 28
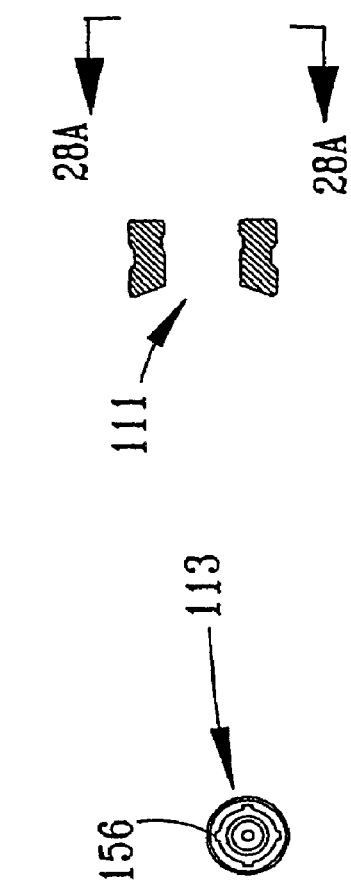
FIG. 26
FIG. 27A

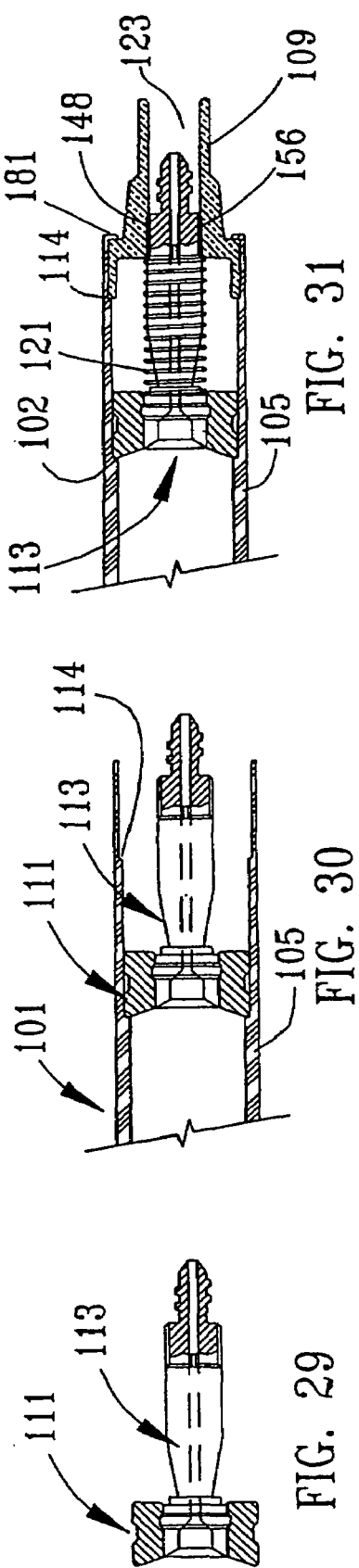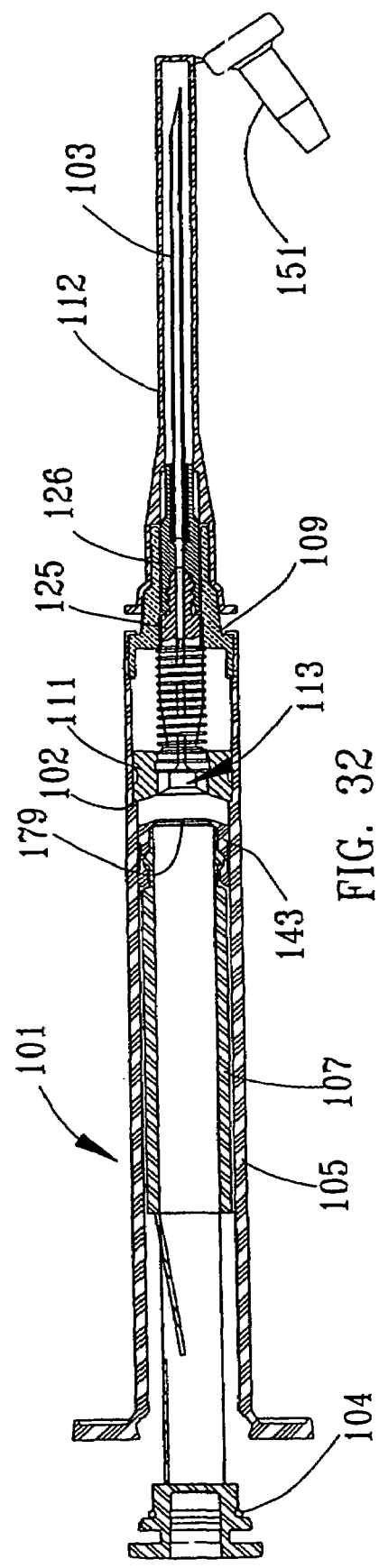

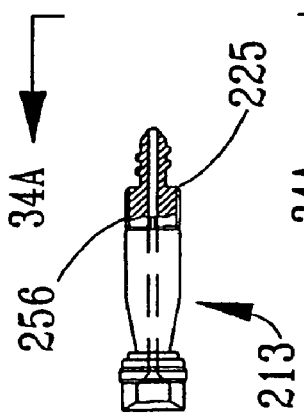
FIG. 34
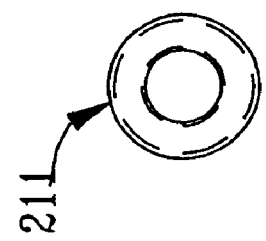
FIG. 35A
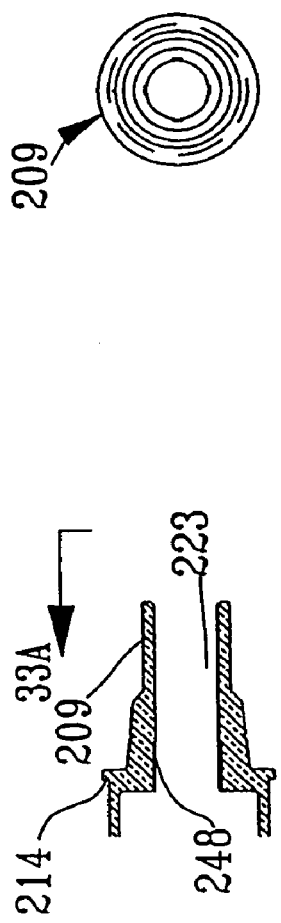
FIG. 33A
FIG. 35
FIG. 33
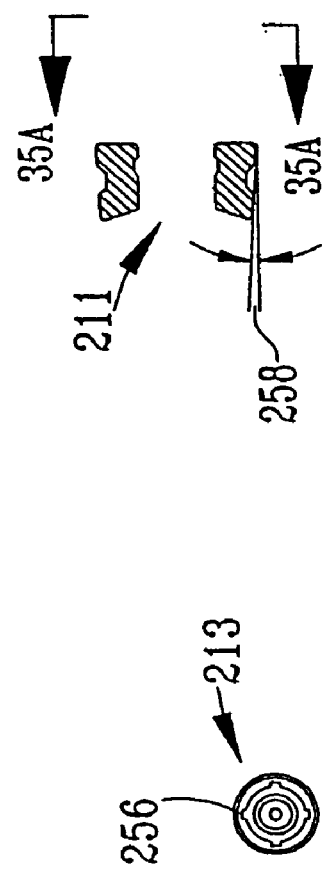
FIG. 34A

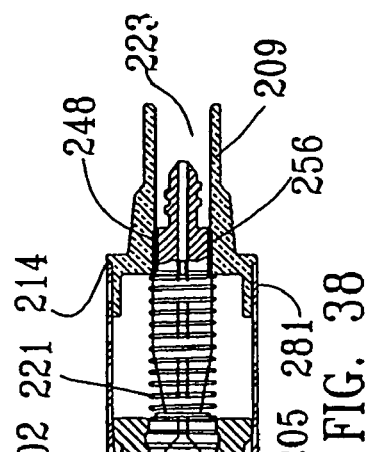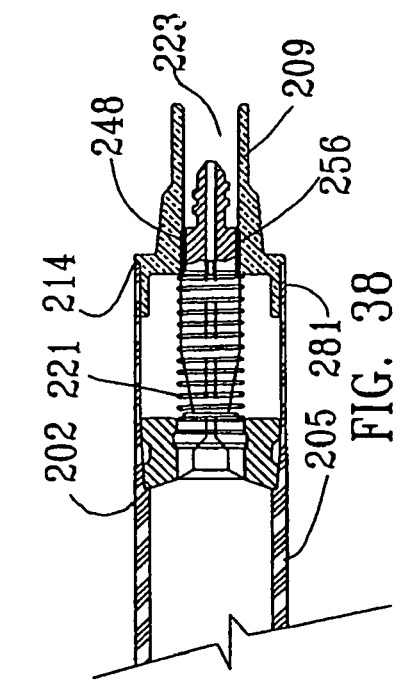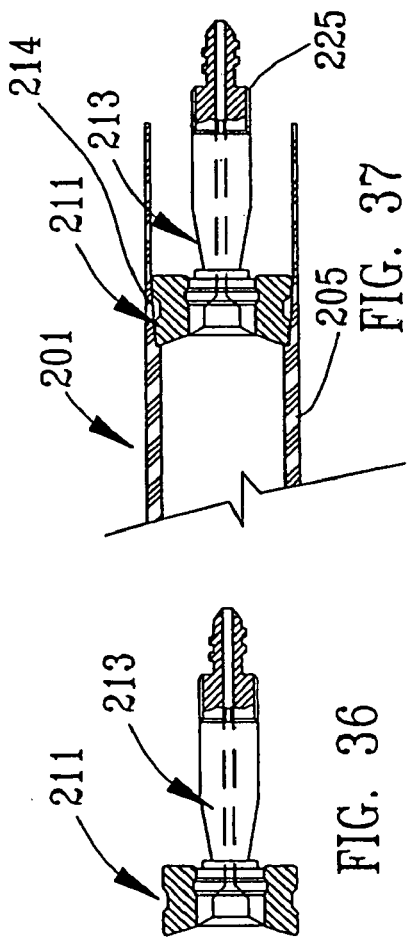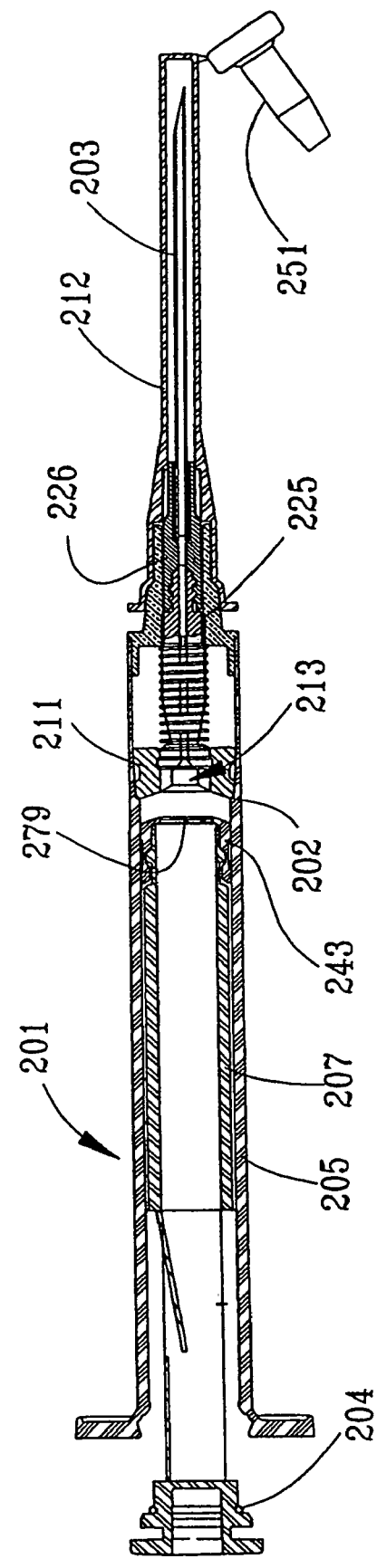

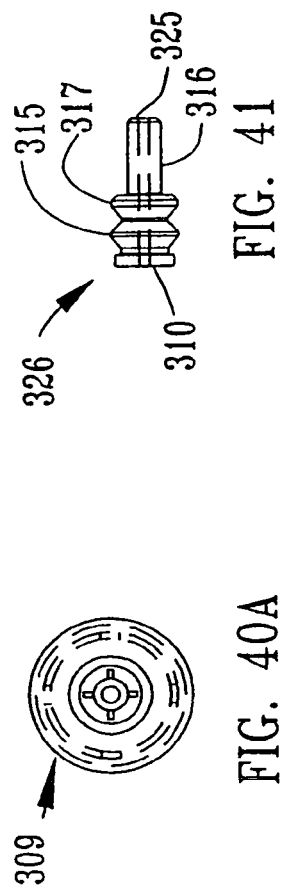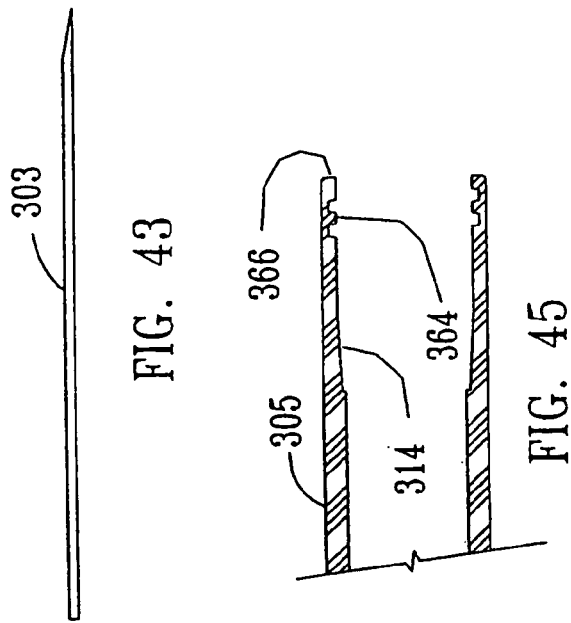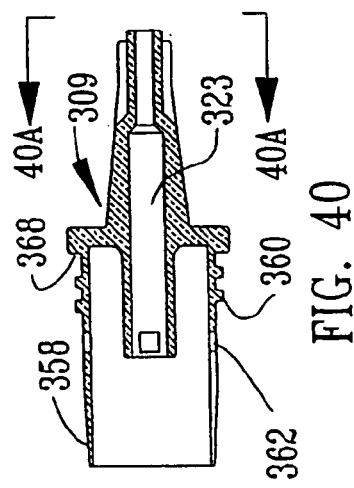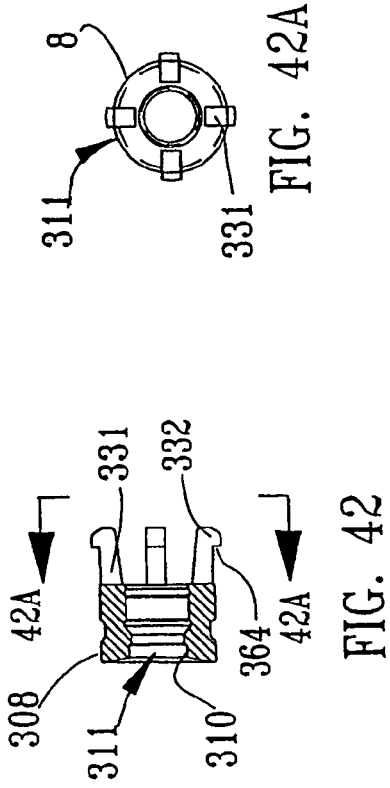

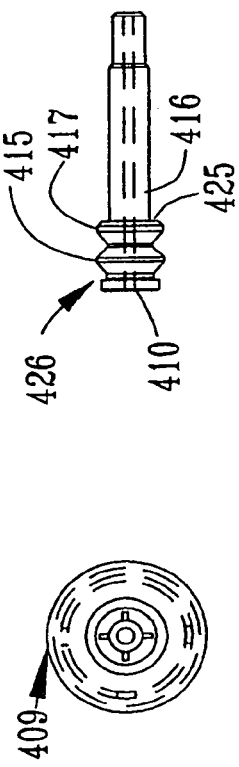
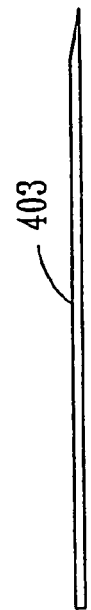
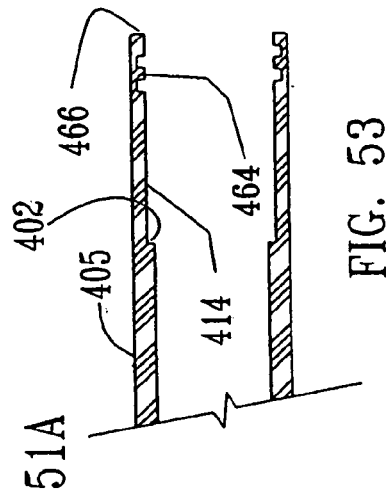
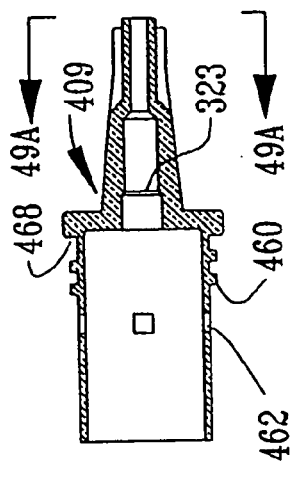
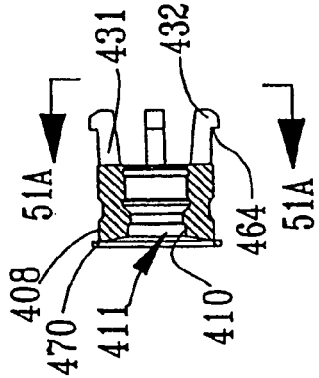

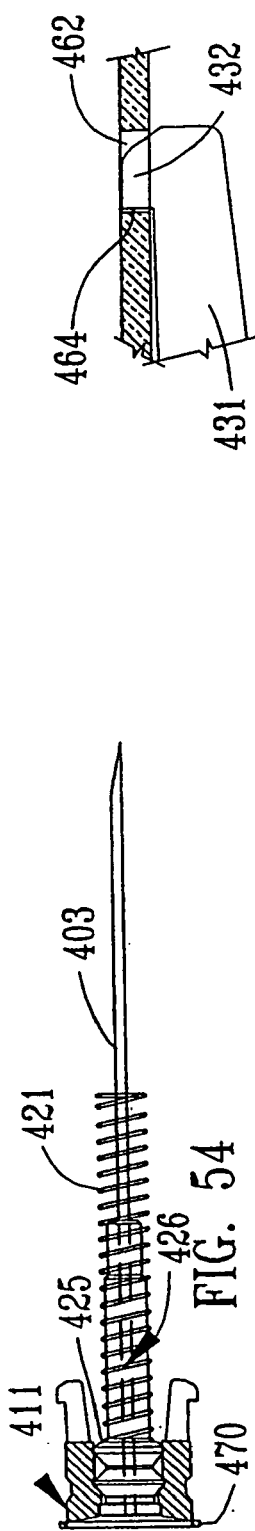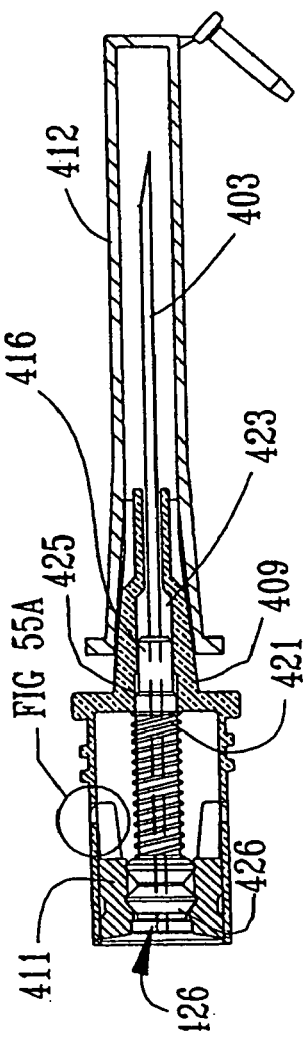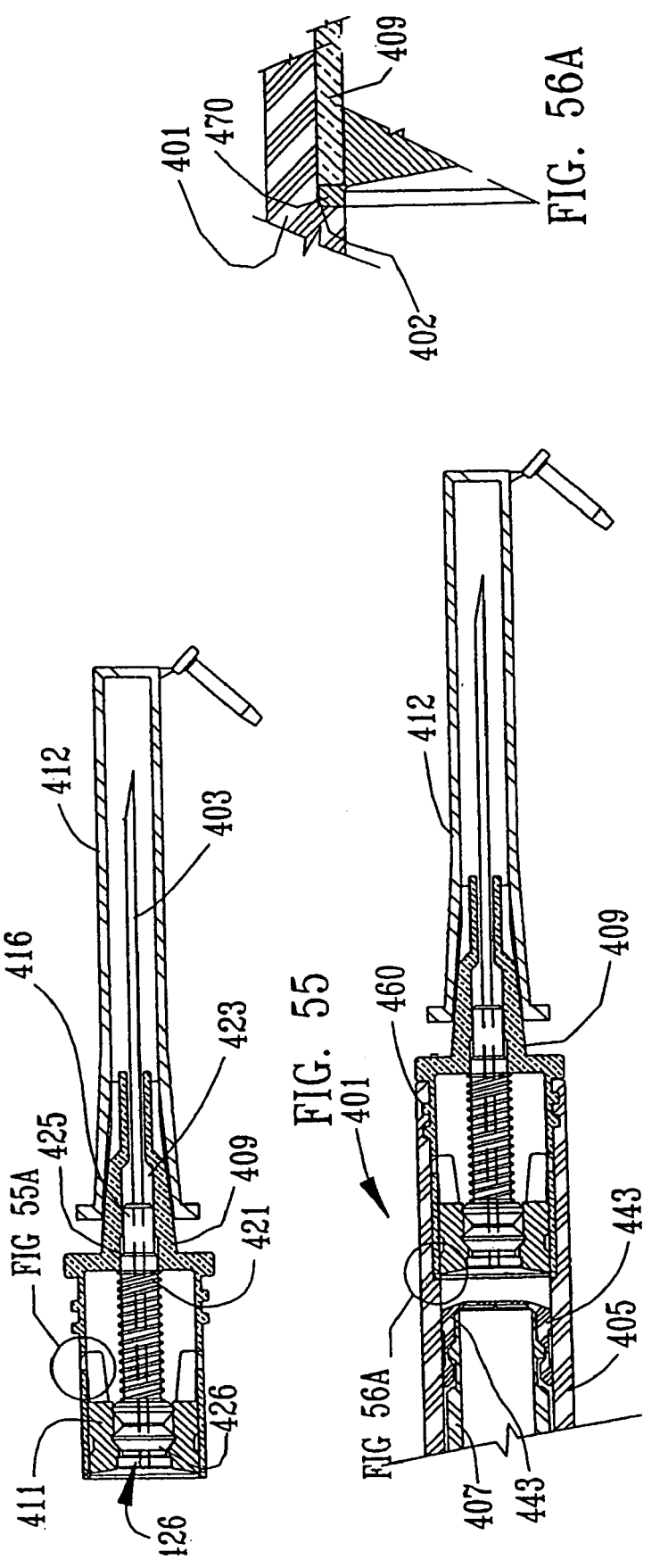

INTERCHANGEABLE NEEDLE SAFETY SYRINGE

RELATED APPLICATIONS

This application claims priority under U.S. law to U.S. Patent Application No. 60/120,622 filed Feb. 18, 1999, entitled "Interchangeable Needle Safety Syringe," which is incorporated by reference herein.

FIELD OF THE INVENTION

This invention relates generally to the art of safety syringes and more particularly to a safety syringe with an interchangeable needle which reduces the likelihood of unintentional puncture or pricking of human skin.

BACKGROUND OF THE INVENTION

In recent history, the transmission of contagious diseases, particularly those brought about exclusively by the co-mingling of human body fluids, has been of great technological interest. One of the particular problems has been associated with the use and disposal of hypodermic syringes, particularly among healthcare professionals. There have been various devices developed for the destruction of the needles or cannula used in such syringes. Additional devices have been developed for capping of syringes, while fixed needle safety syringes have also been designed, all of which attempt to minimize the likelihood of accidental puncture. The accidental puncture or pricking of a finger, or any other part of the body, after the treatment of a patient with a contagious disease, particularly a deadly contagious disease, results in a high likelihood of transmission of that disease. Various syringes have been developed in the prior art to attempt to minimize the likelihood of accidental puncture after patient treatment.

One such device is described in U.S. Pat. No. 4,973,316 to Dysarz wherein a needle is retracted into the barrel of the syringe after the use thereof. Another such device is described in U.S. Pat. No. 4,921,486 to DeChellis, et al.

Other references describing devices relating to needle retraction in a syringe include U.S. Pat. No. 4,994,034 to Bostich et al., U.S. Pat. No. 4,838,869 to Allard, and U.S. Pat. No. 5,114,410 to Batlle, GB 2 197 792 to Powers et al., WIPO 90/06146 to Nacci et al., and WIPO 90/03196 to Utterberg et al. Additionally, U.S. Pat. No. 5,407,431 to Bostich, et al, describes a safety syringe with an interchangeable needle. While all such devices seek the same goals of preventing accidental puncture and providing user flexibility, considerable room for improvement exists.

SUMMARY OF THE INVENTION

These as well as other objects are accomplished by a hypodermic syringe having a barrel with a plunger movable therein to inject a fluid through a hollow needle thereof. A hollow needle hub is housed in a passageway within a needle assembly to which is releasably attached a replaceable needle. Positioned between the passageway within the needle assembly and a shelf on an internal wall of the syringe barrel is a deformable base, with integral flexible supports. The deformable base forms a liquid tight seal with the barrel, at the needle end of the barrel. The deformable base houses a head of the needle hub, forms a liquid tight seal with the base, and is in contact with energy storage means within the passageway in the needle assembly. The plunger has a thin, rupturable web on an end thereof which is part of a boot covering the end of the plunger, the boot, including the web, being liquid impermeable for forcing a liquid from the barrel upon movement of the plunger. Upon completion of an injection, the boot covered plunger contacts the deformable base, and upon application of force at the plunger, moves such base downward. Continued application of force causes flexible supports to flex and move over the sidewall of the needle assembly, permitting the deformable base to move the head of the needle hub downward until further movement of the needle hub is blocked by the passageway in the needle assembly. With the needle hub blocked by the passageway, continued force at the plunger causes the deformable base to move around the needle hub. As the deformable base moves further, the needle hub begins to protrude from the deformable base and come into contact with a web on the boot of the plunger.

Continued force causes the head of the needle hub to tear the web of the boot, positioning the needle hub just inside a hollow portion of the plunger. The torn portion of the web creates a flap just inside the hollow plunger. As the plunger moves the deformable base still further, the needle hub eventually looses contact with the deformable base, which triggers a release of energy from the energy storage means in the passageway, projecting the needle hub with its changeable needle attached thereto into the hollow portion of the plunger. Once inside the plunger, the needle hub is trapped by its enlarged head behind a flexible catch within the plunger. Final movement of the plunger causes the plunger to become substantially locked in the barrel and causes a liquid tight seal to be created between the plunger and the syringe body. A closing member placed on the front of the needle assembly completely seals the syringe to prevent residual fluids from escaping. Completion of the needle retraction also automatically highlights an indicia such as a biohazard label which alerts persons handling the device that the syringe has been used and represents a potential biohazard.

In multiple alternative embodiments presented later, various methods are taught to effect changeability of the needle. For these embodiments, concepts of operation of the retractable needle may be substantially the same, or other means of causing the needle to retract may be used. Rather than focusing on the retraction method, these embodiments focus on various ways of allowing needles of varying gauges to be used with same basic syringe body. One embodiment generally accomplishes this by forming a head on the needle that can mate with, in a detachable fashion, a needle hub that is formed as part of the syringe body, simply attached to the syringe body or otherwise associated with the syringe body. By way of example, the needle head may be formed with threads for mating with corresponding threads inside the needle hub. Or, snap-lock ridges may be inscribed on the needle head and needle hub so that the two can mate in a locking fashion. Many different mating connections can be used, so long as the needle head can be detachably inserted into the needle hub without causing the spring or other propellant means to trigger during the installation process. In other words, one cannot require substantial force for detachably inserting and removing the different sizes and types of needles because otherwise the act of interchanging needles will cause the syringe to trigger, this rendering it useless.

Other methods may be used for forming an interchangeable needle while accomplishing this objective. For instance, in stead of simply inserting the head into a mating needle hub, the needle hub itself could be detachably connected to the syringe body. This would allow the user simply to unscrew one complete needle hub assembly and replace it with another. One advantage to this approach is that the needle hub could be formed so as completely to contain the mechanism for restraining the needle against the bias of the spring or other propelling means. Another advantage is that the assembled needle hub and needles may be larger and thus easier for the user to deal with than simply just another gauge needle. Additionally, because the needle hub can be formed with a ledge or the like to support a needle guard that will surround the needle before use and prevent sharps injuries, one can leave a guard on the needle hub while installing the entire assembly onto the rest of the syringe body.

This invention accordingly aims to provide a hypodermic safety syringe having one, more or combinations of the following advantages:

- the ability to minimize the likelihood of accidental puncture.
- the ability to use an interchangeable needle, before syringe utilization, for selection of the optimum needle type and gauge for patient procedures and effectiveness and to provide a syringe which also provides automatic indication that the syringe represents a biohazard after utilization.
- the ability to, after utilization with a patient, captures and isolates the used needle so as to render such needle harmless.
- the ability to a hypodermic syringe which is operable utilizing only one hand.
- to provide such a syringe which automatically, upon the end of an injection, retracts the interchanged needle to prevent its reuse, while sealing the needle within the body of the syringe to prevent leakage of residual fluids.
- to provide a simple device, which is manufacturable in high volumes.

BRIEF DESCRIPTION OF THE DRAWINGS

FIG. 1 is a cross-sectional view illustrating a completed assembly of the needle hub, base, barrel, needle assembly, and energy storage means of a syringe of this invention.

FIG. 2 is a sectional view of a replaceable needle head and needle of this invention.

FIG. 2A is an enlarged view of the encircled area in FIG. 2.

FIG. 3 is a sectional view of a replaceable needle head and a filter needle of this invention.

FIG. 4 is a sectional view of an alternative embodiment of a replaceable needle head and needle of this invention.

FIG. 5 is an isolated sectional view of the barrel of this invention.

FIG. 5A is a cross-sectional view along line 5A—5A of FIG. 5.

FIG. 6 is a side view of the needle hub.

FIGS. 6A, 6B, and 6C are enlarged partial side views of the end of the needle hub of this invention illustrating alternate embodiments of sealing mechanisms.

FIG. 7 of the drawings is an elevational side view of the energy storage means.

FIG. 8 is a cross-sectional subassembly view illustrating the assembly of the needle hub and base.

FIGS. 16, 17, 18, 19, 20, 21, 22, 23, 24, and 24A are cross-sectional views of the syringe of this invention showing the sequence of operation, after the injection cycle.

FIGS. 26, 26A, 27, 27A, 28, 28A, 29, 30, 31, and 32 are sectional views of an alternative embodiment of the interchangeable needle head and needle and subassembly of the needle hub, base, barrel, needle assembly, and energy storage means of a syringe of this invention, where no supports are utilized in the subassembly and the needle hub is blocked in the passageway.

FIGS. 33, 33A, 34, 34A, 35, 35A, 36, 37, 38, and 39 are sectional views of another alternative embodiment of the interchangeable needle head and needle and subassembly of the needle hub, base, barrel, needle subassembly, and energy storage means of a syringe of this invention, where no base supports are utilized in the subassembly, a shelf on the needle assembly contacts the end of the barrel, a taper on the base mates with a taper in the body, and is blocked in the needle hub in the needle assembly.

FIGS. 40, 40A, 41, 42, 42A, 43, 44, 45, 46, 47, 47A, and 48 are sectional views of an alternative embodiment showing a replaceable nose and needle assembly cooperating with an assembly of the needle hub, base, barrel, needle assembly, and energy storage means of a syringe of this invention.

FIGS. 49, 49A, 50, 51, 51A, 52, 53, 54, 55, 55A, 56 and 56A are sectional views of an alternative embodiment of a replaceable nose and needle assembly and subassembly of the needle hub, base, barrel, needle assembly, and energy storage means of a syringe of this invention.

DETAILED DESCRIPTION OF THE INVENTION

Figure 9:
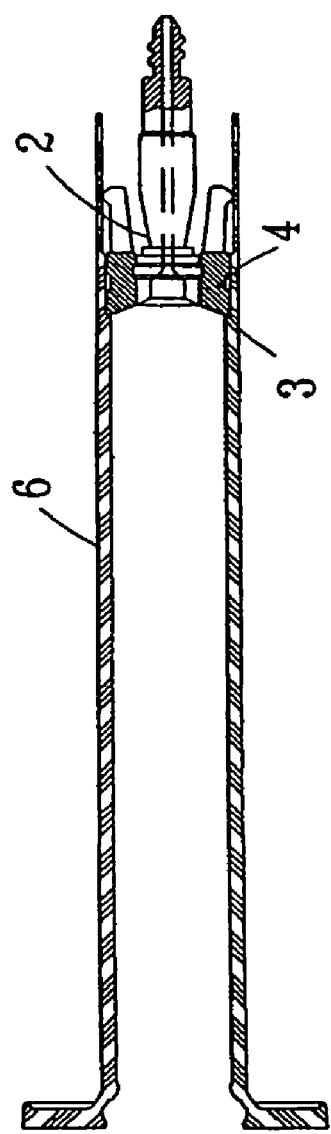
FIG. 9 is a cross-sectional subassembly view illustrating the assembly of the needle hub, base, and barrel.

Before describing the drawings and embodiments in more detail, several terms are described below in an effort to clarify the terminology used in this document. Additional and fuller understanding of these terms will be clear to persons skilled in this art upon reading this entire document:

"Needle assembly": refers to the area on the end of the syringe in which the needle, spring or base are assembled. The needle assembly can be a separate, physical piece that is attached to or associated with the rest of the syringe body. Alternatively, the needle assembly could be just the section of the syringe body near which the needle, spring, or base are partially or completely located.

"Needle head": refers to the end of the needle that is associated with the syringe and which has an enlarged area. The enlarged area may be formed as part of the needle itself, or may be an additional piece fitted to the needle end. The enlarged area may be formed of plastics, metal or other suitable materials.

"Needle hub": refers to a device that mates with the needle head. The device may be a separate, generally elongated device placed in the needle assembly area between, e.g. a base an one end of the needle assembly. Alternatively, the needle hub may be formed as part of the base, needle assembly or other component located in that area.

"Attached to": means that physical parts are actually attached, possibly with an intermediate member between them, either by welding, gluing, snap-lock fit, screws or other attachment mechanisms known in the art. The attachment is designed to be semi-permanent in that the user does not normally remove the physical parts that are said to be attached.

"Associated with": means that the devices in question are permanently or detachably coupled. Associated with is intended to be broader in scope than "attached to," and covers devices that users may or may not be able to remove.

In accordance with this invention it has been found that a syringe may be provided for normal operation which permits changing a needle subsequent to use, but which, upon completion of normal operation and continued movement of a plunger, results in a triggering of a needle hub with the interchangeable needle to project such needle harmlessly into the plunger and body of the syringe.

Once trapped inside the plunger and body of the syringe, the needle is no longer subject to accidental pricking or poking of human tissue thus minimizing the likelihood of transfer of a contagious disease which may be carried by fluids contained on the surface of or within such needle. To prevent possible leakage of residual fluids in the needle, the syringe is sealed after use, and after such use an automatic indication is given that the syringe represents a biohazard. Various other advantages and features will become apparent from a reading of the following description given with reference to the various figures of drawing.

FIG. 1 is a cross-sectional view illustrating a subassembly of a needle hub 2, base 4, barrel 6, needle assembly 8 and an energy storage means 10 of a syringe 1 (shown in FIG. 13) of this invention in a normal pre-injection position. In a preferred embodiment, energy storage means is a spring 10. Base 4 is shown as a deformable body, but could be formed of multiple pieces, e.g. one piece that is deformable (such as an o-ring or the like) and others rigid. Needle assembly 8 is affixed to the barrel 6 by guiding the threaded end of needle hub 2 through the center of passageway 15 and inserting needle assembly 8 into the front of barrel 6, until mating shelf 17 on needle assembly 8 contacts and is positioned against the top edge of the barrel 6. Permanent joining between the needle assembly 8 and the barrel 6 can be accomplished by ultrasonic welding around the circumference of barrel 6 at overlap 7 between the two parts, or any other permanent attaching means can be used. Attachment of the needle assembly 8 to the barrel 6 creates a liquid tight seal between the two parts. As a result of this assembly step, the end of the needle assembly 8 is positioned just in contact with engaging flanges 19 of supports 21 thus preventing movement of the base 4 and the needle hub 2 contained therein for normal syringe use. If the needle hub 2 is formed as part of a single molded syringe barrel 6, then the needle head 2 could be molded with a ridge or the like against which flanges 19 could bear. A preferred material for the base 4 is an elastomer. Supports 21 are illustrated in the preferred embodiment as a pair of opposing semicircular cantilevered beams, however, it is envisioned according to this invention that supports 21 could be connected and unitary, divided up further, or in some embodiments, be eliminated all together.

FIG. 2 shows a sectional view of a replaceable needle head 12 and needle 14 of this invention. Fixed and sealed into a cavity 13 of the needle head 12 is the needle 14 by means of adhesive 16, or other means of fixing needle hub 2 to needle head 12. Female threads 18 are illustrated for releasably attaching, or detaching, the needle head 12 to the needle hub 2, fixed within the passageway 15 of the needle assembly 8. A bevel 20 of the needle head 12 mates with a bevel 22 in the needle hub 2 to create a liquid tight seal between the two parts. Alternate embodiments of sealing mechanisms are illustrated in FIGS. 6A, 6B, and 6C. Fins 23 on needle head 12 (as shown in FIG. 2) mate with slots 25 in a needle guard 27 as seen in FIG. 14, which releasably fix the needle guard 27 to the needle head 12 and prevent rotation of needle head 12 in the needle guard 27.

This invention provides for releasably attaching a variety of types and styles of needles to the needle hub 2 within the passageway 15 because the configuration of the needle hub 2 and needle head 12 remain constant and allow mating of needles 14 of various lengths and features to the syringe 1. For example, needles 14 ranging from a 18 gauge to a 26 gauge of various lengths may be used with this invention. Additionally, filter needles which are not intended to be retractable work with this invention as prescribed in standard syringe practice. Moreover, the interchangeable needle safety syringes of this invention may be compatible with syringes of other manufacturers including those made by Retractable Technologies and New Medical Technologies, Inc.

FIG. 2A is an enlarged view of the encircled area of FIG. 2 showing fins 23 and recess 29 on fin 23 used for releasably fixing the needle guard to the needle head 12.

FIG. 3 shows a sectional view of a replaceable needle head 26 and a filter needle 24. Adhesive 28 or other satisfactory means binds the needle 24 to the needle head 26. A filter 30 is positioned between the needle 24 and the needle head 26 to protect from any debris entering the barrel during the syringe fill cycle. The uncontaminated filter needle is not retracted into the syringe but is removed and thrown away after use and replaced by another replaceable needle which is generally retractable.

FIG. 4 is an alternative embodiment of a needle 14 disposed within the needle head 12. The needle head 12 is the same as the needle head 12 shown in FIG. 2. FIG. 4 shows an example of a different length and gauge needle 14, where the needle shaft is shorter than the needle shaft shown in FIG. 2.

FIG. 5 shows an isolated section view of the barrel 6. FIG. 5A is a cross-sectional view along line 5A—5A of FIG. 5 showing a finger support flange 40 of the barrel 6 of this invention. Referring to FIGS. 5 and 5A, an undercut 42 for locking the plunger into the barrel is shown at the finger support flange 40 of barrel 6. At the opposite end of the barrel 6, a base shelf 3 and a base relief shelf 44 are illustrated. These internal offsets receive the base in the case of shelf 3, while the function of the shelf 44, is to provide room for base expansion as the base 4 is deformed and travels over hub 2 during operation.

FIG. 6 shows an isolated view of the needle hub 2. Top 46, flange 48, spring contactor 50, hub catch receiver 52 and hub block 54 are illustrated. Needle hub 2 male threads 56 and bevel 22 are also illustrated and are used to releasably attach the needle head 12 to needle hub 2, while also creating a liquid tight seal between the two parts.

FIGS. 6A, 6B, and 6C illustrate alternate embodiments for sealing mechanisms of needle hub 2 to the needle head. FIGS. 6A and 6B represent seals 51 and 53 formed as integral and unitary parts of the needle hub 2, while FIG. 6C illustrates seal 55 as an O-ring seal.

FIG. 7 is an elevational view of the energy storage means 21 illustrated as a spring 10.

FIG. 8 shows an assembly step accomplished by inserting the needle hub 2 into the base 4. Once inserted, a base wedge 58 is positioned for a substantially mating engagement over a flange 48 of the needle hub 2 which blocks needle hub 2 movement in both directions when inserted in the barrel 6. A liquid tight seal between the needle hub 2 and a needle hub seal 60 on the base 4 as shown in FIG. 8 is created at the needle hub 2. With the needle hub 2 blocked into the base 4, the next assembly step is accomplished.

FIG. 9 shows the next step of the assembly process, where the subassembly in FIG. 8 is inserted into the front end of the barrel 6 as shown in FIG. 9, until the base 4 contacts and is positioned against the base shelf 3. When the base 4 is completely inserted as shown in FIG. 9, the base 4 is compressed circumferentially in the direction of the needle hub 2, and a liquid tight seal is produced between the base 4 and the barrel 6, and needle hub 2 is restrained from movement.

Figure 10A:
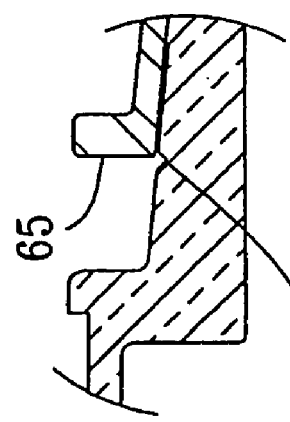
FIG. 10A is an isolated sectional view of the guard edge of the needle guard.
Figure 10:
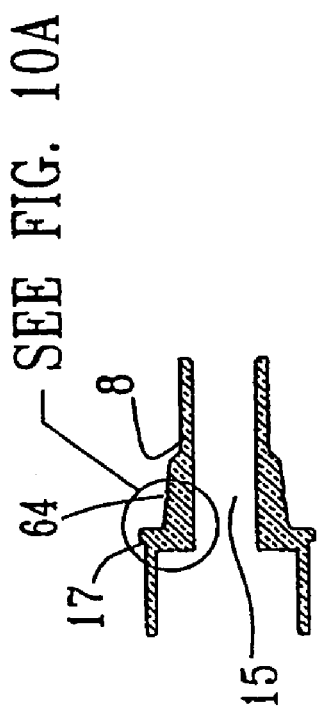
FIG. 10 is isolated sectional view of the needle assembly of this invention.

FIG. 10 shows an isolated sectional view of the needle assembly 8 of this invention. The passageway 15 is shown and is defined within the needle assembly 8. A circular grove 64 on the needle assembly 8 serves as a guide for positioning the needle head 12. A rotating shelf 17 contacts and is positioned against the edge of the barrel 6. In an alternative embodiment, the needle assembly 8 is transparent providing for viewing a joint between the needle hub 2 and the needle head 12 after the needle 14 is changed.

FIG. 10A shows the circular groove 64 on the needle assembly 8 that serves as an indicator that needle head 12 is in proper position when a guard edge 65 on the guard 27 (shown in FIG. 14) is over the center of the groove 64.

Figure 11:
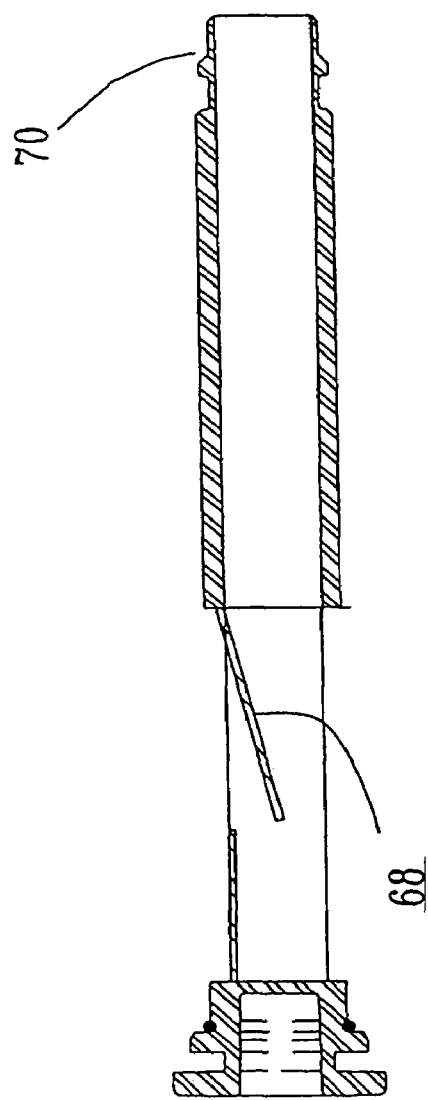
FIG. 11 is an isolated sectional view of a plunger in accordance with this invention.

FIG. 11 of the drawings is an isolated sectional view of a plunger 66 in accordance with this invention. A capturing means 68 is illustrated for capturing the needle hub 2 with interchangeable needle 14 attached thereto into hollow 82 of plunger 66. A plunger boot termination 70 is also illustrated and is designed to receive and mate with rupturable boot 72.

Figure 12:
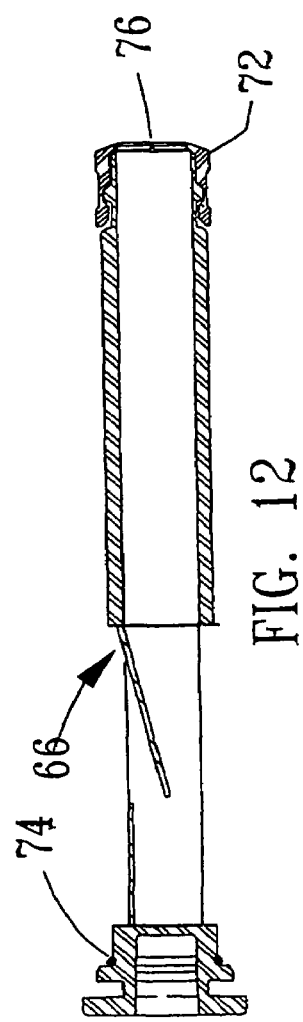
FIG. 12 is a cross-sectional view of the plunger of this invention, showing assembly of the plunger boot and the plunger seal on the plunger.

A plunger seal 74 and the boot 72 are placed onto the plunger 66 as shown in FIG. 12. The boot 72 is preferably placed onto plunger 66 so that a web 76 is just at the end of the plunger.

The plunger 66 is then inserted into the barrel 6. The thickness of the web 76 and the tear grooves are selected to withstand normal operating pressures within the syringe 1, yet allow relative ease in the puncturing of the web 76 by the needle hub 2. The preferred material for boot 72 is an elastomer. In an alternative embodiment, the seal 74 is formed as an integral and unitary part of the plunger 66 so that the seal as provided by use of an O ring is obviated, and the seal is accomplished by forming the ring as an integral part of the plunger 66.

Figure 13:
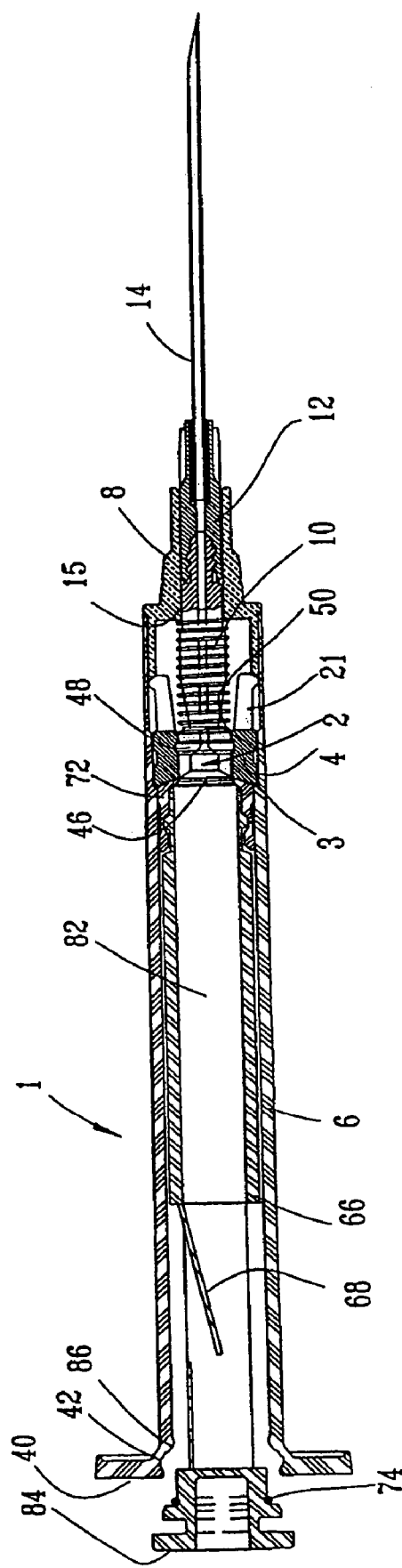
FIG. 13 is a cross-sectional view of the syringe of this invention in an operable pre-activation state.

FIG. 13 is a cross-sectional view of the syringe 1 of this invention in an operable pre-injection state. Operation of the assembled syringe is discussed below. The syringe 1 has a barrel 6 and the plunger 66 mounted therein. The interchangeable needle 14 is contained within the needle assembly 8, which is fixed to barrel 6 by ultrasonic welding means or other permanent attaching means.

The interchangeable needle 14 has the needle head 12 that is releasably fixed to the needle hub 2. The needle hub 2 is generally cylindrical in shape and positioned within and engaged by the deformable base 4. The hub 2 has a top 46 which is preferably concave and diametrically cylindrical. The top of enlarged needle hub 2 can be flat in some embodiments. Below the top 46 on needle hub 2 is a diametrically wider area or flange illustrated by 48 in FIG. 13, which is slightly wider than top 46. In some embodiments there are a plurality of diametrically wider areas or gradually extending flanges illustrated as areas 315 and 317 in FIG. 41 and areas 415 and 417 in FIG. 50. The back of needle hub 2 is defined by a plurality of decreasing diameter steps. The steps closest to top 46 defines contacting portion 50 for contacting the energy storage means 10. By appropriately positioning the needle hub 2 within deformable base 4 for a substantially mating engagement, the arrangement of top 46 and flange 48 of needle hub 2 can be substantially mated and held within deformable base 4 so that a liquid tight seal between needle hub 2 and deformable base 4 is created.

The needle assembly 8 has contained therein the energy storage means, illustrated as spring 10 at the top of a passageway 15, which is in contact with contacting portion 50 of the needle hub 2. The deformable base 4 is positioned between the base shelf 3 on the barrel 6 and one end of the needle assembly 8 wherein the supports 21 of the base 4 contact the wall of the needle assembly 8.

Further referencing FIG. 13, the plunger 66 has a hollow 82 therein and has the boot 72 covering an end thereof which is fluid impermeable for forced movement of a fluid in the barrel 6 during ordinary injection. A portion of the boot 72 is illustrated as having been torn by needle hub 2 in FIG. 22, with the boot web 79 laying to the side in the hollow of plunger 66.

Preferably, the plunger 66 has an enlarged thumb push 84 which, upon completion of a compression stroke, is substantially locked within recess 42 in the syringe body 6 by a mating head portion 94 of barrel 6 (shown in FIG. 24A).

FIG. 14 shows a side view of the needle guard 27, with a needle assembly closing member 90 tethered at the end thereof. The closing member 90 is attached or tethered by a breakable tab 92 which can be of plastic construction and which is broken to remove the closing member 90. As illustrated, the closing member 90 is preferably a plug which is attached by the tab 92 to the needle guard 27 at an angle wherein the tab 92 connects to the closing member 90 away from the end of the closing member 90 which can be inserted or plugged into the opening of the needle assembly 8 left after needle retraction. As discussed above, the closing member 90 of this invention can be of various types, such as a cap or a plug as shown, as long as the opening left by needle retraction can be closed. Preferably the opening is closed off so that a liquid tight seal is obtained. The angular attachment of the closing member 90 preferred herein and illustrated in FIG. 14 allows a person completing needle retraction to handle just the needle guard 27 to insert the closing member 90 into the needle assembly 8 where the needle 14 was positioned prior to retraction. Quite advantageously, this can be accomplished with the user's hands always position behind the opening in the needle assembly 8 left as a result of needle retraction.

Figure 14A:
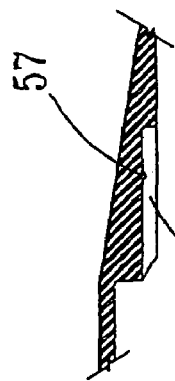
FIG. 14A is an enlarged view of the encircled area of FIG. 14.
Figure 14:
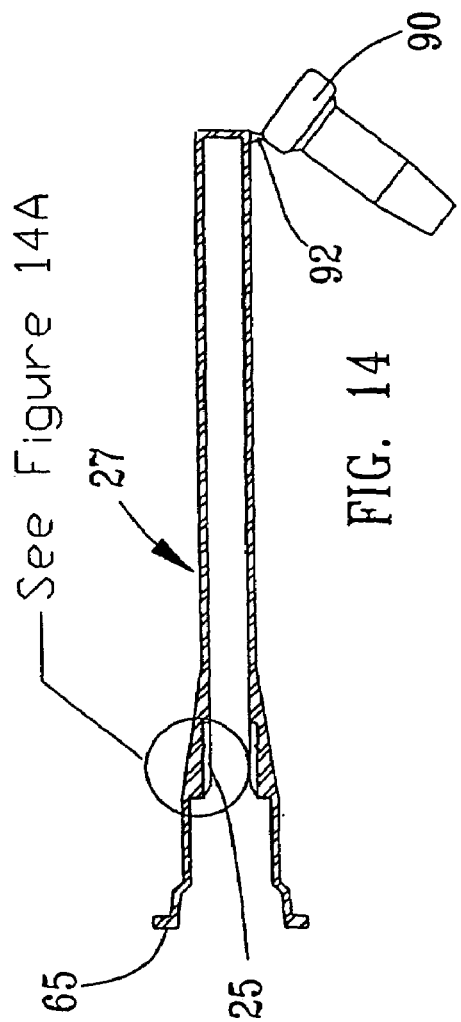
FIG. 14 is an elevational view of the needle guard, showing the needle assembly closing member tethered, for example, to the tip of the needle guard.

FIG. 14A is an enlarged view of the encircled area of FIG. 14 showing slot 25 and bead 57, used in conjunction with recess 29 (shown in FIG. 2A) for releasably fixing the needle head with its needle into the guard.

Figure 15:
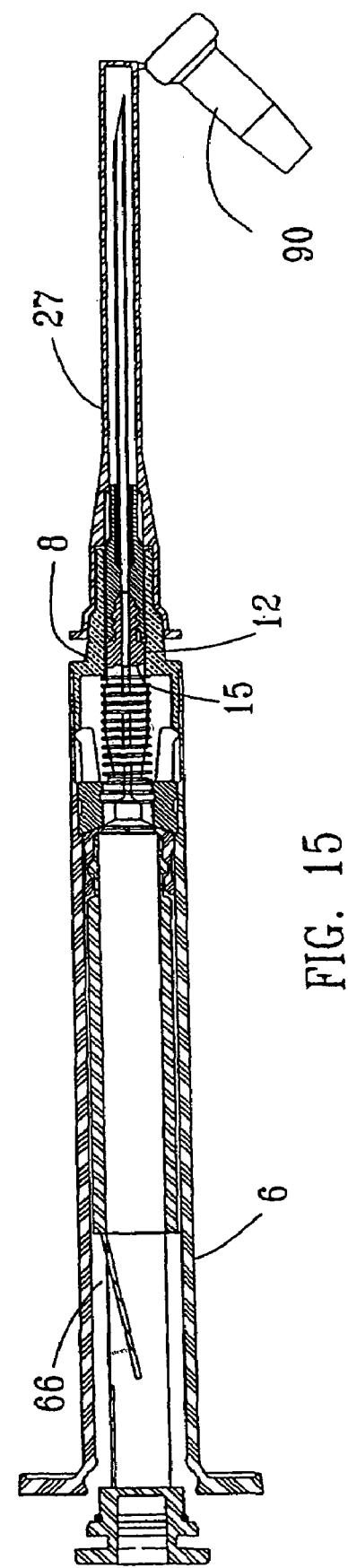
FIG. 15 is a cross sectional view of the completed assembly of the syringe, including the needle guard.

FIG. 15 shows the needle guard 27 placed on the needle head 12, with the needle assembly closing member 90 tethered at the tip of needle guard 27. The guard is placed into its position by snapping bead 57 shown in drawing 14A into recess 29 on fin 23 shown in drawing 2A. Fins 23 on needle head 12 as seen in FIG. 2 mate with slots 25 in guard 27 as shown in FIG. 14 and releasably fix the guard 27 to the needle head 12 and prevent rotation of the needle head 12 in the needle guard 27. As depicted in FIG. 15, the needle head 12 has been inserted into the open end of the passageway 15 of the needle assembly 8. Female mating threads 20 on the needle head 12 (as shown in FIG. 2) are guided by the passageway 15 into the male threads 22 on the needle hub 2 (as seen in FIG. 6). The needle guard 27 with needle head 12 and its needle 14 releasably fixed therein has been twisted until the needle head 12 is substantially fixed to the needle hub 2 and a liquid tight seal is formed between the two parts, thus completing the assembly process. The circular groove 64 on the needle assembly 8 (shown in FIGS. 10 and 10A) serves as an indicator that the needle head 12 is in the proper position when the guard edge 65 (shown in FIG. 10A) on the needle guard 27 is over the center of the groove 64.

It will be apparent to those in the art that there exists other possible sequences of assembly other than those described that can be used to produce the completed assembly as shown in FIG. 15, producing the same syringe ready for operation.

FIGS. 16 through 24 show the sequence of operation of the interchangeable needle safety syringe 1 and will now be described with reference to FIG. 13 and FIGS. 16 through 24. As can be seen, FIG. 13 is a cross-sectional view of safety syringe 1. For normal syringe operating forces, the safety syringe 1 operates as any conventional syringe. For use, the syringe 1 is filled from an ampule in a normal manner, as standard procedure dictates. Once filled, the injection cycle is accomplished, again according to standard practice. At completion of the injection cycle, the plunger boot 72 is just mating with the base 4, as shown in FIG. 16, and all fluids, which can be, are expended from syringe 1. Before the syringe is released, or discarded, by the user, the needle retraction cycle should be accomplished.

At the beginning of the needle retraction cycle, the syringe 1 is usually held between the index finger and the middle finger at the support flange 40, with the thumb resting on thumb push 84, presumably the same as the syringe was held at completion of the injection cycle. The plunger 66 is just mated with the base 4 at the boot 72, as shown in FIG. 16.

With reference to FIG. 17, force is applied between the finger support flange 40 and the thumb push 84. This force is transmitted along the plunger 66 to the deformable base 4 and the supports 21. As the force increases sufficiently, the supports 21 be in to flex and close towards one another as shown in FIG. 17, forcing the flange 19 to ride up on the interior wall of the needle assembly 8 thus allowing further forward movement of the base 4 and needle hub 2 with the interchangeable needle 14 contained therein.

As shown in FIG. 18 the continued application of force applied at the plunger 66 continues to cause the supports 21 to ride up on the interior wall of the needle assembly 8, and as the deformable base 4 moves further, energy storage means 10 is further compressed. The deformable base 4 moves forward until a hub block 54, on needle hub 2 which is in translation with the base 4, comes into contact with the top of the passageway 15, preventing further movement of hub 2. This allows the plunger 66 to force the base 4 to deform and pass around the now stationary needle hub 2.

With reference now to FIG. 19 as the deformable base 4 moves further toward the end of the barrel 6, the needle hub 2 begins to protrude from the base 4 and come into contact with and stretch the web 76 of the boot 72 on the plunger 66. Continued force causes further translation of the base 4 and the needle hub 2 to tear web 76 of the boot 72, positioning the needle hub 2 just inside hollow 82 of the plunger 66 while the flange 48 on the needle hub 2 remains embedded within deformable base 4, as shown in FIG. 19. As the base 4 moves forward in the barrel 6 and transverses the barrel shelf 44 which effectively increases the inter-diameter of barrel 6, holding forces on the needle hub 2 as a result of circumferential compression of the base 4 in the narrower part of barrel 6 is diminished, facilitating release of the needle hub 2 from the base 4.

With reference to FIG. 20, continued translation of the deformable base 4 causes the flange 48 to eventually lose contact with the deformable base 4, creating a trigger-like release of the needle hub 2. Upon this trigger-type action, energy stored within the energy storage means 10 is released and imparted to the needle hub 2 to project the needle hub 2 and the replaceable needle 14 into the hollow 82 of the plunger 66, as illustrated in FIG. 21.

Referring now to FIG. 22, it is seen that the needle hub 2, at its top 46, contacts a capturing means 68 which elastically flexes to permit the needle hub 2 to pass through the constriction formed by the capturing means 68 and the interwall of the barrel 6. This is further illustrated in FIG. 23 where the needle hub 2 with replaceable needle 14 is shown having passed the capturing means 68 and captured within the hollow 82 of the plunger 66 where in the head of the needle hub 2 has moved back past the capturing means 68. At this point, it should be noted that the plunger 66 has been substantially locked within recess 42 of the barrel 6, by a mating head portion 94 engaging a portion of the plunger 66 near a thumb push 84, as shown in FIG. 24A. A liquid tight seal between a plunger seal 79 and a guard ring 86 is created.

To finish the operational sequence, the closing member 90, tethered to the end of the needle guard 27, can be inserted into opening 22 of the needle assembly 8, as shown in FIGS. 23 and 24. The closing member 90 is forced into position by pressing the front of the syringe against a heavy, solid object. Once the closing member 90 is lodged into position, the closing member 90 can be separated from the needle guard 27 with a twisting action, leaving syringe 1 as shown in FIG. 24. This closure process can therefore be advantageously accomplished with a user's hands always remaining behind the opening left by the retracted replaceable needle. As a result of accomplishing the needle retraction cycle, syringe 1 is left as shown in FIG. 24.

Figure 25:
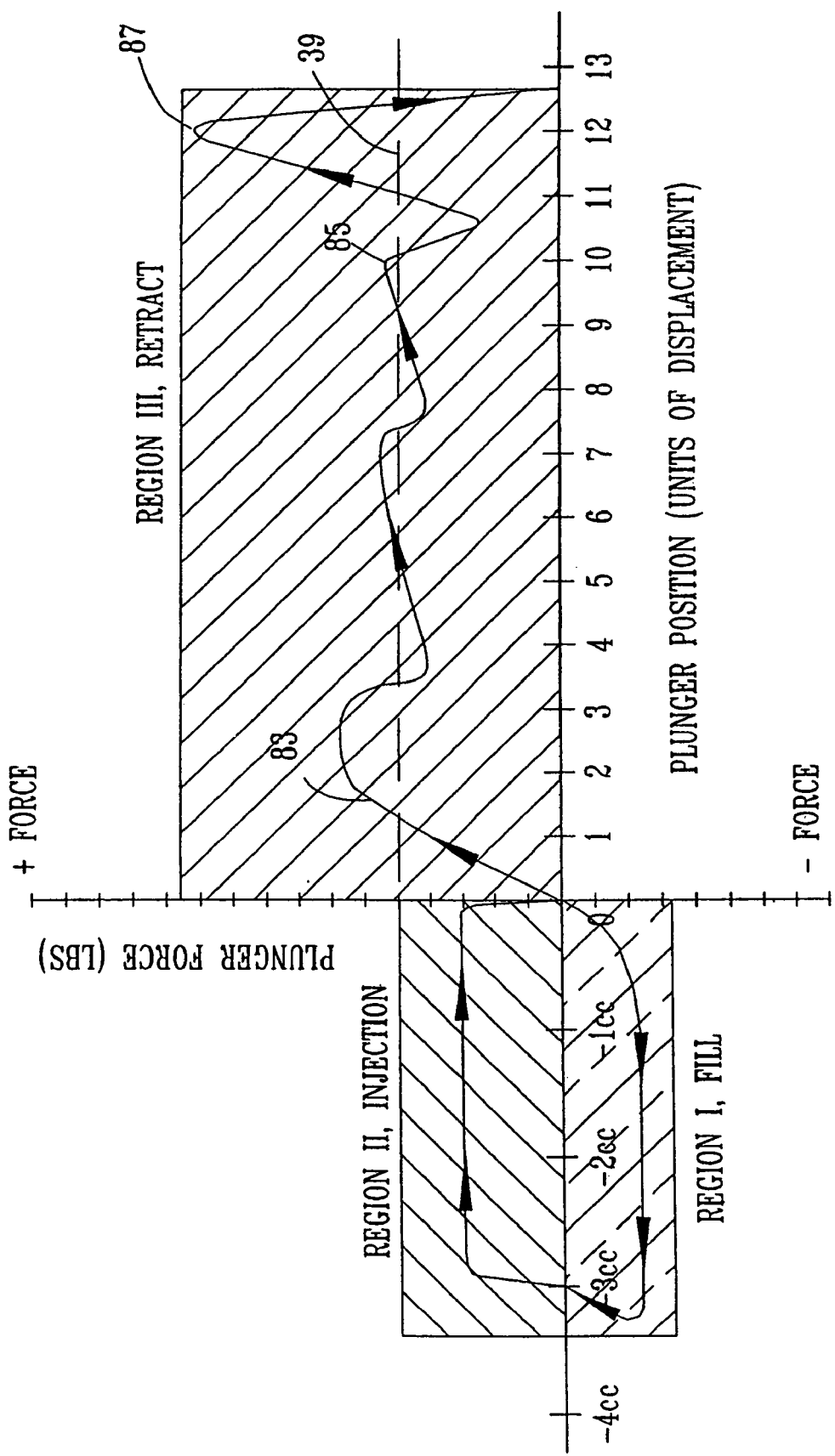
FIG. 25 is a graph depicting the Force/Balance relationship upon which the syringe operation is based.

The syringe operates on a "Force/Balance" principal as depicted in the graph of FIG. 25. In the graph normal operation is represented by regions I and II. In these regions limited positive and negative forces are applied between the plunger 66 and the body 6, shown in FIG. 15, for normal operating functions of filling the syringe and for injections. Positive forces are defined as forces which move the plunger 66 into the syringe body 6, while negative forces are defined as forces which pull the plunger 66 from the syringe body 6.

Typical "filling" and "injection" cycles are depicted in regions I and II, respectively. As long as the positive force applied between the plunger 66 and body 6 of syringe 1 is below threshold 39, the base 4 balances the operating force and remains in its assembled position, as shown in FIG. 15. But, for positive forces applied to the syringe above threshold 39, the base 4 becomes unbalanced and begins to move in the direction of needle assembly 8. Once force above threshold 39 is applied and maintained, operation of the syringe moves into region III, where the needle is retracted into the plunger of the syringe. In FIG. 25, the item numbers "83", "85", and "87," in region III of the graph respectively refer to where in a typical device the base 4 first begins to move, the needle hub 2 is released and the plunger 66 becomes substantially locked into the body 6.

At least four alternative embodiments are envisioned for the syringe invention defined herein. FIGS. 26 through 32 define alternate embodiment 1 as syringe 101, FIGS. 33 through 39 describe alternate embodiment 2 as syringe 201, FIGS. 40 through 48 describe alternate embodiment 3 as syringe 301, and FIGS. 49 through 56A describe alternate embodiment 4 as syringe 401. Each of the embodiments is substantially similar in operation to syringe 1, and as such differences between alternate embodiments and syringe 1 will be defined.

FIGS. 26 through 32 show sectional views of an alternative embodiment of the replaceable needle head and needle, cooperating with an assembly of a needle hub, base, barrel, needle assembly, and spring, where no supports are utilized. With reference to FIGS. 26 through 32, components of syringe 101 that are different from syringe 1 taught herein are needle assembly 109, needle hub 113, base 111, and body 105. With reference to the figures, FIG. 26 is an isolated sectional view of the needle assembly 109 of this invention showing locking slots 148 at the entrance of and recessed into the side wall of a passageway 123, which extend part way through the passageway 123. FIG. 26A is a cross sectional view of the needle assembly 109 along line 26A—26A of FIG. 26 showing a front view of the needle assembly 109. FIG. 27 of the drawings is an isolated view of the needle hub 113 showing locking bars 156 which extend radially out from the sidewall of the needle hub 113. FIG. 27A is a cross sectional view of the needle hub 113 along line 27A—27A showing a front view of locking bars 156. FIG. 28 is an isolated sectional view illustrating the base 111, wherein flexible supports have been eliminated. Assembly of syringe 101 is accomplished in similar manner to syringe 1. First, as shown in FIG. 29, the needle hub 113 is inserted into and matingly held in the base 111. The base 111 and the needle hub 113 are next inserted into the front of the body 105, until the base 111 comes into contact with the barrel shelf 102 as shown in FIG. 31. Placing the base 111 into body 105 circumferentially compresses the base onto the needle hub 113, prevents movement of the needle hub 113 in the base 111, and insures that a liquid tight seal between the needle hub 113 and the base 111, and the base 111 and the body 105 is obtained.

With reference to FIG. 31, a spring 121 is placed over the needle hub 113. The needle assembly 109 is next guided onto the needle hub 113 such that the outwardly radially extending locking bars 156 on the sides of the needle hub 113 are mating with and engaged into locking slots 148 in the passageway 123 on the needle assembly 109. The needle assembly 109 is next pushed into the open end of body 105, which compresses spring 121, until the sidewall of the needle assembly 109 bottoms out on the barrel shelf 114. The needle assembly 109 is then permanently fixed to body 105 by heat staking techniques at position 181 as shown in FIG. 31, or other suitable permanent fixing means. With the needle assembly positioned into the body 105 as shown in FIG. 32, a hub block 125 (as shown in FIG. 27) just contacts the bottom of locking slots 148 in the passageway 123 (as shown in FIG. 26), thus restricting further movement of the needle hub 113 into the passageway. In the opposite direction the needle hub 113 is restrained from movement by mating engagement with the base 111, which is blocked by the barrel shelf 102. With reference to FIG. 32, the next step of the assembly process is accomplished by placing the boot 143 and a plunger seal 104 on plunger 107, and inserting the plunger 107 into body 105 as illustrated in FIG. 32. Before insertion of the plunger 107 into body 105, it is common manufacturing practice to lubricate the interior wall of body 105. Silicon is usually the lubricant of choice for this application. Assembly is completed by placing the needle head 126 which is held in a needle guard 112 (in identical manner to syringe 1) into the open end of the needle assembly 109 and twisting the needle head 126 onto the needle hub 113, which completes the assembly process. Rotation of needle hub 113 is prevented by interlocking bars 156 within slots 148, as depicted in FIG. 31. Operation of syringe 101 is substantially the same as for syringe 1, with one exception in that needle hub 113 is fixed in passageway 123 and initial forward movement of the needle hub 113 during the needle retraction cycle is prevented.

With reference to FIGS. 33 through 39, an alternative embodiment of a syringe 201 having a replaceable needle is shown. With reference to the figures, FIG. 33 is an isolated sectional view of a needle assembly 209 of this invention showing locking slots 248 at the entrance of and recessed into the side wall of a passageway 223, which extend part way through the passageway 223. FIG. 33A is a cross sectional view of the needle assembly 209 along line 33A-33A of FIG. 33 showing a front view of the needle assembly 209. FIG. 34 of the drawings is an isolated view of a needle hub 213 showing locking bars 256 which extend radially out from the sidewall of the needle hub 213. FIG. 34A is a cross sectional view of the is needle hub 213 along line 34A—34A showing a front view further illustrating locking bars 256. FIG. 35 is an isolated sectional view illustrating a base 211, wherein flexible supports have been eliminated and a taper 256 along the length of the base 211 is illustrated. Assembly of syringe 201 is accomplished in similar manner to syringe 1 and syringe 101.

Referring to FIGS. 36, 37 and 38, the needle hub 213 is first inserted into and matingly held in the base 211. The base 211 and the needle hub 213 are next inserted into the front of body 205, until the base 211 comes into contact with the barrel shelf 202.

Placing the base 211 into body 205 circumferentially compresses the base 211 onto hub 213, prevents movement of the hub 213 in the base 211, and insures that a liquid tight seal between the hub 213 and the base 211 and the base 211 and the body 205 is obtained. A spring 221 is placed over the needle hub 213. The needle assembly 209 is next guided onto the needle hub 213 such that the outwardly extending locking bars 256 on the sides of the needle hub 213 (seen in FIG. 34) are mating with and engaged into locking slots 248 in passageway 223 on the needle assembly 209 (as seen in FIG. 33). The needle assembly 209 is next pushed into the open end of body 205, which compresses spring 221, until the top edge of the body 205 bottoms out on the needle assembly shelf 214. The needle assembly 209 is then permanently fixed to body 205 by ultrasonic welding techniques at position 281 as shown in FIG. 38, or other suitable permanent fixing means. With reference to FIG. 39 the needle assembly 209 positioned into the body 205, a hub block 225 just contacts the bottom of locking slots 248 in the passageway 223 (as shown in FIG. 33) thus restricting further movement of the needle hub 213 into the passageway. In the opposite direction hub 213 is restrained from movement by mating engagement with the base 211, which is blocked by a barrel shelf 202. The next step of the assembly process is accomplished by placing a boot 243 and a plunger seal 204 on the plunger 207, and inserting the plunger 207 into body 205 as illustrated in FIG. 39. It is common manufacturing practice to lubricate the interior wall of the body 205, usually with silicon, before insertion of plunger 207 into body 205. Assembly is completed by placing needle head 226 and needle 203 which is held in a needle guard 212 (in identical manner to syringe 1) into the open end of the needle assembly 209 and twisting needle head 226 onto the needle hub 213, which completes the assembly process. Rotation of the needle hub 213 is prevented by interlocking bars 256 and slots 248, as depicted in FIGS. 33 and 34. Operation of syringe 201 is substantially the same as for syringe 1, with two exceptions. First, needle hub 213 is fixed into passageway 223 and initial forward movement of needle hub 213 during the needle retraction cycle is prevented, and secondly, as base 211 moves forward during the retraction cycle, mating tapers between the two parts spread, providing space at the body for the base to more easily deform around needle hub 213.

With reference to FIGS. 40 through 48, components of syringe 301 that are different from syringe 1 taught herein is a replaceable nose and needle cooperating with a body 305.

With reference to the figures, FIG. 40 is an isolated sectional view of a needle assembly 309 of this embodiment of the invention showing the base retainer slots 362, positioned at various points on the exterior sidewall of the needle assembly 309, and threads 360, also positioned on the exterior sidewall of the needle assembly 309. FIG. 40A is a cross sectional view of the needle assembly 309 along line 40A—40A of FIG. 40 showing a front view of the needle assembly 309. FIG. 41 of the drawings is an isolated view of a needle head 326 showing diametrically larger areas 315 and 317 than top 310, and a spring contact 325, as described for syringe 1. FIG. 42 is an isolated sectional view of a base 311 illustrating the mating cavity for needle head 326 and flexible supports 331, with support flange 332. Also, illustrated are the base retainer catches 364 positioned on the back side of support flange 332. FIG. 42A is a cross sectional view of the base 311 along line 42A—42A showing an end view of the base 311. FIG. 43 is an isolated view of needle 303, while FIG. 44 is an illustration of spring 321. FIG. 45 is a partial isolated sectional view of body 305 showing a taper 314 and mating threads 364. Assembly of syringe 301 is accomplished in similar manner to syringe 1.

Figure 47A:
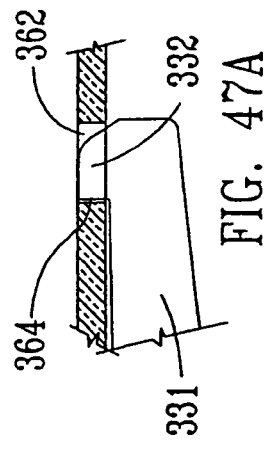
Figure 46:
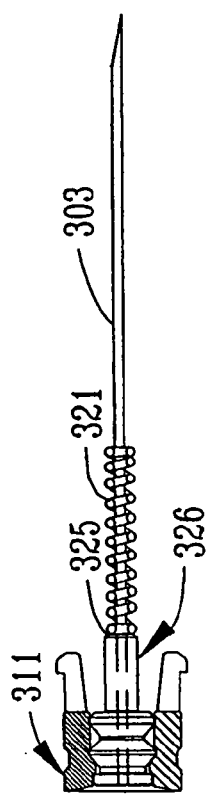
Figure 47:
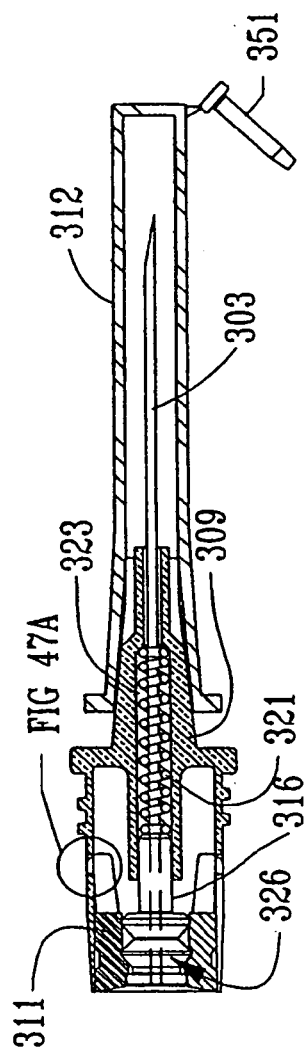
Figure 48:
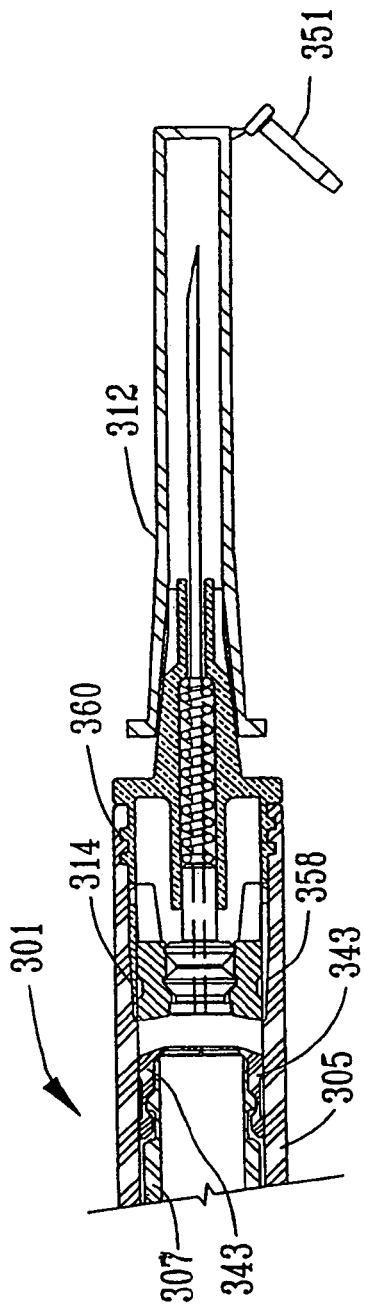

Referring to FIGS. 46, 47 47A, and 48, the needle head 326, with the needle 303 mounted therein, is first inserted into the base mating cavity and held therein by the base 311 as indicated in FIG. 46. The spring 321 is placed over needle 303, until contact with a spring contact 325 is made. The sub-assembly consisting of a base 311, spring 321, and needle head 326 is next inserted into the back of the needle assembly 309, by guiding the needle 303 into and through a passageway 323 of the needle assembly 309 as shown in FIG. 47. The needle assembly 309 is next rotated relative to the base 311 to match the base retainer slots 362 on the needle assembly 309 with retainer catches 364 on the base 311 (as shown in FIGS. 47 and 47A). When the two parts are in alignment, the base 311 is forced into the needle assembly 309, partially compressing spring 321 and placing a shaft 316 of needle head 326 into passageway 323. Insertion of the subassembly into the needle assembly 309 is continued until base retainer catches 364 are latched into the base retainer slots 362, as illustrated in FIG. 47A. Once base retainer catches 364 are positioned into slots 362, position of base 311, and therefore needle head 326, is restrained in both directions. In the one direction movement is restrained by the base catch, while movement of the base 311 and the needle head 326 in the opposite direction is restrained by the flange 332 against the opposite side of the base retainer slot 362 and the force of the spring 321 on the needle head 326 at a spring contact 325. Placing the base 311 into the needle assembly 309 also circumferentially compresses the base 311 between the needle head 326 and the body 305 which insures that a liquid tight seal between needle head 326 and the base 311, and the base 311 and the body 305 is established. The needle guard 312 is next placed on the subassembly, and the resulting completed assembly illustrated in FIG. 47 represents the replaceable needle embodiment of syringe 301. The replaceable needle 303 can then be attached to, or removed from, the body 305 by inserting the base 311 end of the assembly into the open end of the body 305 and threading the assembly into position with the needle guard 312, until top 366 of body 305 (as shown in FIG. 45) mates with flat area 368 on the needle assembly 309 (shown in FIG. 40). In this position, a taper 314 on body 305 substantially mates with a taper 358 on the needle assembly 309 as shown in FIG. 48 to form a liquid tight seal between the two parts. To remove the needle assembly from the body 305, the process described above is reversed. Operation of syringe 301 is substantially the same as for syringe 1.

With reference to FIGS. 49 through 56A, an alternative embodiment syringe 401 having a replaceable nose and needle cooperating with a body 405 is shown. With reference to the figures, FIG. 54 is an isolated sectional view of a needle assembly 409 of this embodiment of the invention showing base retainer slots 462, positioned at various points on the exterior sidewall of the needle assembly 409, and threads 460, also positioned on the exterior sidewall of the needle assembly 409. FIG. 49A is a cross sectional view of the needle assembly 409 along line 49A—49A of FIG. 49 showing a front view of the needle assembly 409. FIG. 50 of the drawings is an isolated view of a needle head 426 showing diametrically larger areas 415 and 417 than top 410, and a spring contact 425, as described for syringe 1. FIG. 51 is an isolated sectional view of base 411 illustrating the mating cavity for the needle head 426 and flexible supports 431, with a support flange 432. Also, illustrated are base retainer catches 464 positioned on the back side of the support flange 432. At the front of base 411 is molded a sacrificial seal 470 used to seal the needle assembly 409 with body 405. FIG. 51A is a cross sectional view of the base 411 along line 51A—51A showing an end view of the base 411, further illustrating a seal 470. FIG. 52 is an isolated view of the needle 403. FIG. 53 is a partial isolated sectional view of body 405 showing receiving surface 414 for the needle assembly 409, mating threads 464, and shelf 402. Assembly of the syringe 401 is accomplished in similar manner to syringe 1 and syringe 301. Referring to FIGS. 54, 55, 55A, 56, and 56A, the needle head 426, with the needle 403 mounted therein, is first inserted into the base 411 mating cavity and held therein by the base 411 as indicated in FIG. 54. The spring 421 is placed over the needle hub 426, until contact with a spring contact 425 is made. The sub-assembly consisting of base 411, spring 421, and needle head 426 in FIG. 54 is next inserted into the back of the needle assembly 409 as shown in FIG. 55, by guiding needle 403 into and through passageway 423 of the needle assembly 409. The needle assembly 409 is next rotated relative to base 411 to match base retainer slots 462 on the needle assembly with retainer catches 464 on the base. When the two parts are in alignment, base 411 is forced into the needle assembly 409, substantially compressing the spring 421 and placing shaft 416 of the needle head 426 into the passageway 423.

Insertion of the subassembly into the needle assembly 409 is continued until base retainer catches 464 are latched into the base retainer slots 462, as illustrated in FIG. 55a. With the base 411 locked into the needle assembly 409, a sacrificial seal 470 is positioned at the back edge of the needle assembly 409. Once the base retainer catches 464 are positioned into slots 462, position of the base 411, and therefore the needle head 426, is restrained in both directions. In the one direction movement is restrained by the base catch 464, while movement of the base 411 and the needle head 426 in the opposite direction is restrained by the flange 432 against the opposite side of the base retainer slot 462 and the force of spring 421 acting on the needle head at the spring contact 425.

Placing the base 411 into the needle assembly 409 also circumferentially compresses the base between needle head 426 and body 405 which insures that a liquid tight seal between needle head 426 and the base 411, and the base 411 and the body 405 is established. The needle guard 412 is next placed on the sub-assembly, and the resulting completed assembly illustrated in FIG. 55 represents the replaceable needle embodiment of syringe 401. The replaceable needle 403 can then be attached to, or removed from, the body 405 by inserting the base end of the assembly into the open end of the body 405 and threading the assembly into position with a guard 412, until top 466 of body 405 (as shown in FIG. 53) mates with flat area 468 on the needle assembly 409 as shown in FIG. 49. In this position, the sacrificial seal 470 is compressed between the body 405 at shelf 402 and needle assembly 409 as shown in FIG. 56A to form a liquid tight seal between the two parts. To remove the needle assembly 409 from the body 405, the process described above is reversed. Operation of syringe 401 is substantially the same as for syringe 1.

Figure 57:
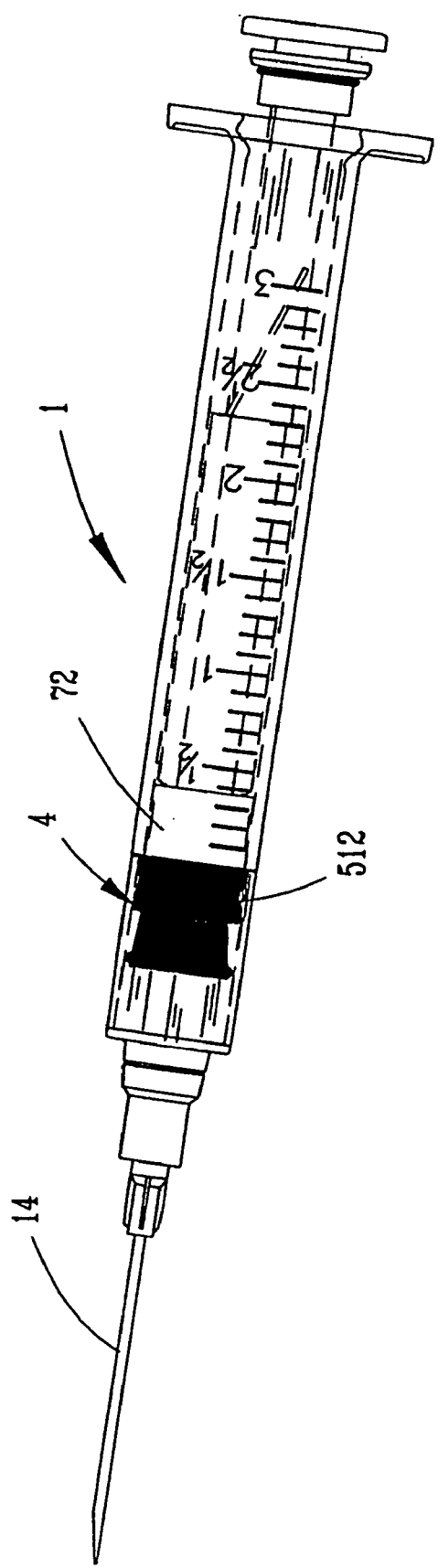
FIG. 57 is an elevational view of the syringe prior to needle retraction.
Figure 58:
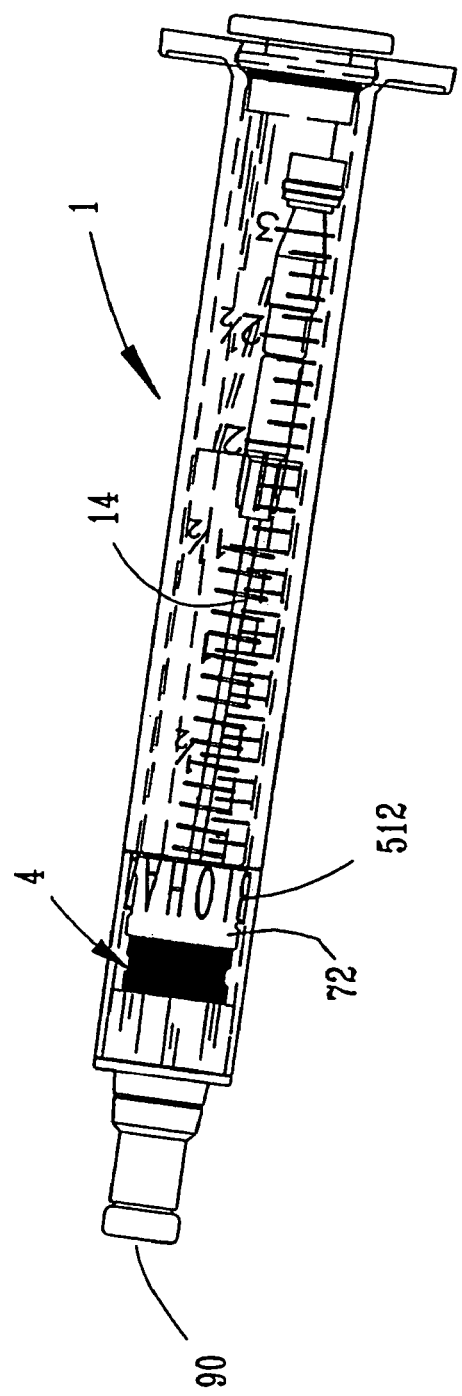
FIG. 58 is an elevational view of the syringe subsequent to needle retraction wherein an indicia has been revealed.

FIGS. 57 and 58 show an elevational view of the syringe 1 before and after needle retraction wherein an indicia has been revealed. During the needle retraction cycle revelation and amplification of an indicia or label such as biohazard label 512, as shown in FIG. 58. Before the needle retraction cycle, the base 4 is under biohazard label 512 as seen in FIG. 57 where in the label is not readable. It is preferred that biohazard label 512 be printed in black, or any other appropriate color, and base 4 also be the same or substantially similar color so that biohazard label 512 is unnoticeable to the user. It is also preferred that the boot 72 be of a different, contrasting color. After the needle retraction cycle, the base 4 is no longer left under the biohazard label, and the boot 72 is under the label as shown is FIG. 58. Since the plunger boot 72 is any appropriate highly contrasting color relative to the base 4 and the biohazard label 512, such as orange when the other two are black, the biohazard label 512 is significantly revealed and amplified and becomes very noticeable to the user or other people, as shown in FIG. 58.

It is thus seen that this invention with the illustrative alternative embodiments provides a novel syringe apparatus which has a needle that interchangeable and is operable by a single hand and which upon completion of injection captures the utilized interchangeable needle and renders such harmless within the plunger of the syringe. Further, such used syringe is rendered liquid tight to prevent possible leakage of contaminated fluids and such used syringe is automatically marked as a biohazard. As various other advantages and features will become apparent to those of skill in the art from a reading of the foregoing description which is exemplary in nature, such modification and variations are embodied within the scope of this invention.

What is claimed is:

1. A safety syringe comprising:
  a) an interchangeable needle;
  b) an elongated barrel having first and second ends, a needle hub defining a plurality of radially extending bars in mated engagement with a corresponding slot defined by an interior wall of a passageway defined by a needle assembly, the interchangeable needle attached to a threaded first end of said needle hub;
  c) a plunger sized and shaped to be received in the second end of the barrel and to be moveable therein;
  d) a moveable base adapted to releasably constrain said needle hub, said moveable base adapted for slideable movement of said moveable base and said needle hub within an interior of said elongated barrel and in the direction of said first end of said barrel;
  e) a spring, at least partially compressed, said spring positioned entirely within the barrel and surrounding a portion of said needle hub between a base of said needle hub and said threaded first end of said needle hub, said spring adapted to bias the interchangeable needle within the barrel; and
  f) at least one support member having a first end and a second end, said support member positioned within said barrel, said first end of said support member engaging said moveable base and a second end engaging an edge of a needle assembly, said needle assembly edge positioned along an interior wall of said barrel, said at least one support member further surrounding an axial portion of each of said needle hub and said partially compressed spring;
  wherein the plunger is moved within the barrel applying force to the interchangeable needle and causing the spring to retract the needle hub and associated interchangeable needle within the plunger.

2. A safety syringe comprising:
  a) an interchangeable needle;
  b) an elongated barrel having first and second ends, an interior of the barrel defining a tapered wall, an edge of said tapered wall providing a shelf upon which a first end of a moveable base is positioned, the interchangeable needle attached to a threaded first end of a needle hub, a portion of said needle hub positioned within a portion of said elongated barrel;
  c) a plunger sized and shaped to be received in the second end of the barrel and to be moveable therein;
  d) a moveable base adapted to releasably constrain said needle hub, said moveable base adapted for slideable movement of said moveable base and said needle hub within an interior of said elongated barrel and in the direction of said first end of said barrel;
  e) a spring, at least partially compressed, said spring positioned entirely within the barrel and surrounding a portion of said needle hub between a base of said needle hub and said threaded first end of said needle hub, said spring adapted to bias the interchangeable needle within the barrel; and
  f) at least one support member having a first end and a second end, said support member positioned within said barrel, said first end of said support member engaging said moveable base and a second end engaging an edge of a needle assembly, said needle assembly edge positioned along an interior wall of said barrel, said at least one support member further surrounding an axial portion of each of said needle hub and said partially compressed spring;
  wherein the plunger is moved within the barrel applying force to the interchangeable needle and causing the spring to retract the needle hub and associated interchangeable needle within the plunger.

* * * * *